United States Patent [19]

Dick et al.

[11] 3,954,098

[45] May 4, 1976

[54] SYNCHRONIZED MULTIPLE IMAGE TOMOGRAPHIC CARDIOGRAPHY

[76] Inventors: Donald E. Dick, Salina Star Route, Boulder, Colo. 80302; Daniel Cooper, 1320 Wabash St., Denver, Colo. 80220; Ronald E. Hileman, 2680 Stephens, Boulder, Colo. 80303

[22] Filed: Jan. 31, 1975

[21] Appl. No.: 546,043

[52] U.S. Cl. .......................... 128/2.05 Z; 73/67.8 R; 128/2 V
[51] Int. Cl.² .......................................... A61B 10/00
[58] Field of Search .................. 128/2.05 Z, 2.05 R, 128/2 V, 2 R, 2 A; 73/67.7–67.9

[56] References Cited
UNITED STATES PATENTS

| | | | |
|---|---|---|---|
| 3,624,744 | 11/1971 | Munger | 128/2.05 Z |
| 3,777,740 | 12/1973 | Hokanson | 128/2 V |
| 3,778,756 | 12/1973 | Houston et al. | 73/67.7 X |
| 3,864,661 | 2/1975 | Ranalli | 73/67.7 X |

*Primary Examiner*—Kyle L. Howell
*Attorney, Agent, or Firm*—Lane, Aitken, Dunner & Ziems

[57] ABSTRACT

A scan converter storage surface is divided into image spaces corresponding to different points in the heart cycle. Ultrasound echoes from heart structures are plotted in the image spaces by means of special $x$, $y$ sweeps which are offset to the image spaces by timing circuitry. Separate delay and spacing counters allow the first image to be stored at one interval after detection of the ECG R-wave and successive images to be stored at a another uniform interval. An ECG trace is stored in the first image space with cursors indicating the selected image timing. The scan converter is read out to a TV display. During image build-up, the read and write modes alternate. If desired, the TV sweeps to the scan converter may be attenuated and offset to display a single stored image. Images displayed in sequence provide animation. A self test circuit substitutes a fake ECG and writes bars in the scan converter image spaces using TV sweeps for the scan sweeps. The timing circuitry for the normal images gates the video for the bars. All of the timing for the system is derived from a TV composite sync signal and the patient's ECG current.

23 Claims, 25 Drawing Figures

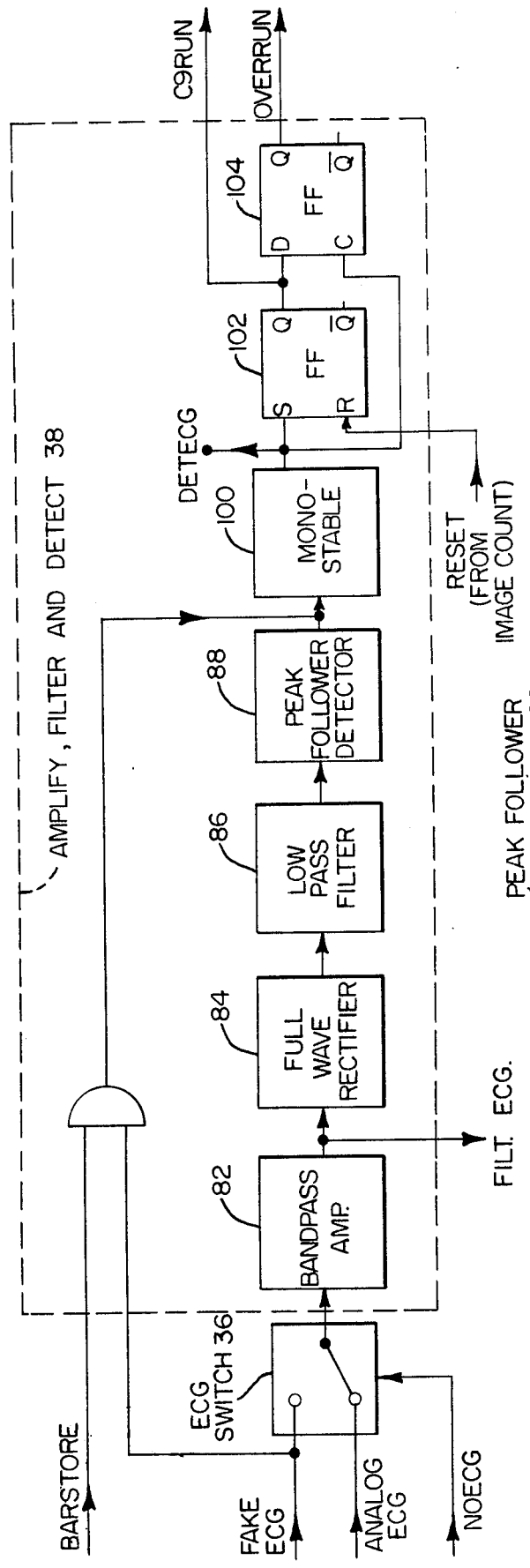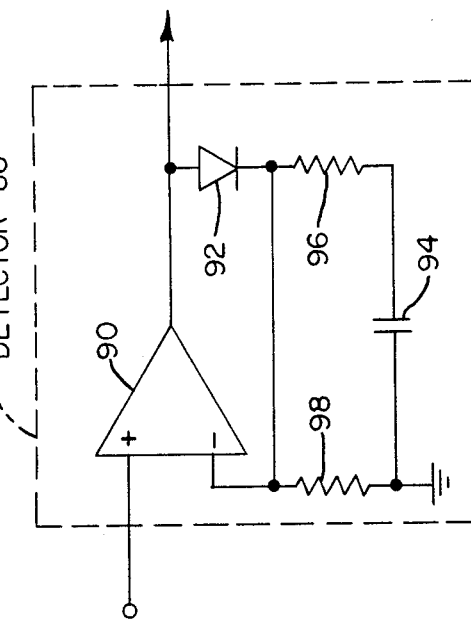

SYNCHRONIZED MULTIPLE IMAGE TOMOGRAPHIC CARDIOGRAPHY

BACKGROUND OF THE INVENTION

The invention relates generally to the field of cardiography and more particularly to the field of synchronized tomographic cardiography especially in ultrasound. The specific embodiment described below uses ultrasonic techniques and it is to the field of ultrasound that this application is primarily directed. However, researchers in the electronics of cardiography will recognize that the principles involved also apply to the fields of nuclear medicine and radiology; that is, the probing medium may be X-rays or gamma-rays, for example, instead of sound.

Few tools could be of greater value in the diagnosis of heart disease than a camera which could take a moving picture of the interior of the heart. However, heart structures cannot be directly differentiated by X-ray techniques, although indirect techniques using X-ray absorbing compounds in the esophagus and blood stream can indicate the general outline of the heart and its cavities. As a practical matter, however, doctors in the past have had to rely primarily on the stethoscope and electrocardiogram (ECG), and to some extent on the angiogram, because there were no direct observational tools available for cardiac diagnosis short of open heart surgery.

Sonar, developed after World War I, lead eventually to the use of sonar principles in nondestructive testing to reveal faults in materials, for example. Nondestructive testing in medicine is called noninvasive diagnosis, and this latter field borrowed the technology of sonar for its own purposes because it was found that the reflectivity of sound can discriminate between adjacent soft tissues.

Ultrasound is sound generated at a frequency above the range of human hearing (20,000 Hz). In medical diagnosis, frequencies around 2 mHz are typical. As in sonar a single transducer acts as both a sender and receiver of ultrasonic energy. The delay which occurs between the emission of pulsed sound and the return of the echo is a direct measure of the distance to the reflecting surface. Under water this means the distance to an energy ship; in the body it means the distance from the chest to the left ventricle of the heart, for example. In contrast, X-ray images reveal the transmissivity of the structures through which the X-rays pass. X-rays show bones well because bone tissue absorbs X-rays much more than soft tissue. On the other hand, ultrasonic systems normally use reflection like sonar although a transmission mode is of course feasible and is used in some circumstances.

Reflection of sound is caused by a difference in the acoustic impedance of adjacent tissues. Because blood and muscle tissues have different acoustic impedances at ultrasonic levels, ultrasound is reflected at the interface between a blood filled cavity and the muscle tissue which defines the cavity. Thus structures like the left ventricle and even the mitral valve of the heart can be detected by ultrasound while these structures do not yield sufficient contrast to differentiate them using x-rays.

The ultrasonic transducer functions like a directional radar antenna in that it defines a narrow beam within which it can transmit energy or receive reflected energy. Hence, in the reception mode sound energy in the vicinity is ignored unless it falls within the narrow beam. Typical beam widths are on the order of 10 millimeters, and typically the depth of the ultrasonic beam need go no farther than 20 centimeters.

The simplest display technique, and therefore the first kind used, for indicating the output of an ultrasonic transducer is to plot the echo output of the transducer versus time on an oscilloscope. If this amplitude mode (A-mode) display were used with a transducer that was properly oriented to intersect the left ventricle, two amplitude peaks corresponding approximately to the known distance to the left ventricle and having a rather large spacing at the end of diastole could be recognized as indicating the width of the left ventricle at that angle of intersection.

Another type of display is the brightness mode (B-mode) where the spacing between colinear dashes indicates the distance between reflecting surfaces. A slow vertical drift with time of the B-mode display results in a motion mode (M-mode). As the transducer is repeatedly pulsed, if the reflecting surfaces undergo periodic movement relative to the direction of the transducer beam, the motion mode will show a plurality of wavy lines.

Until recently the M-mode has been the primary display format for ultrasound cardiography (echocardiography). If the transducer beam intersects a few characteristic structures like the right ventricle, interventricular septum, and left ventricle, the spacing between the wavy lines and the relative motion of the reflecting surfaces which the wavy lines indicate provide dual clues to the identity of the structure being observed. In fact, the M-mode is so good at displaying certain heart structures and functions that it has already become an accepted technique for corroborative diagnosis of mitral stenosis, a valvular heart disease studied by ultrasound to determine the mobility of the mitral leaflet and the presence of calcification. Using the motion mode, medical researchers have also found it possible to study functional outflow tract obstruction and to make planimetric measurements of the left ventricle, for example. While the diagnostic potential of ultrasound remained untapped until recently, the role of ultrasound in cardiology is now rapidly expanding as particular heart diseases are correlated with characteristic echocardiographic abnormalities.

Although A-mode and particularly M-mode display formats have been extremely useful in providing clinical information in the past, there are advantages to a two-dimensional anatomical cardiac imaging system with the capability of demonstrating motion. A-mode and M-mode techniques represent complex waveforms which one can learn to relate to the structures under observation. A two-dimensional imaging technique which pictorially represents these structures draws more freely on the cardiologist's powers of intuitive recognition.

Two dimensional imaging of the heart encounters a specific problem with which A-mode and M-mode displays did not have to cope. Since the heart structures are always in motion, obtaining a two-dimensional image of the heart as if it were at rest requires either (1) scanning much faster than the heart moves or (2) scanning much more slowly with some type of selectivity (gating) in the gathering of information. The rapid scanning technique is exemplified by electronic transducer arrays and by automatic mechanical scanners which move very rapidly.

The other technique is a relatively new one based on stop action sampling in the nature of a stroboscope. An image can be built up one line at a time (i.e., offsetting the transducer beam each time) taking successive sections of data in successive heart beats, but timewise in exactly the same point within each heartbeat. For illustration, if a heart gave 60 beats per minute and a stroboscopic light flashed once a second, the heart would appear motionless because theoretically it would be caught in exactly the same point of the cycle each time the light flashed.

The use of the ECG as a synchronizing device to sample the output of an ultrasonic transducer at the same point within each successive heart cycle is known as the cardiac gate principle. It has been pointed out that gating can be used at different points (phases) of the heart cycle to demonstrate motion of the heart structure. One image of the heart can be formed at the end of diastole and another image of the heart can be formed at the end of systole using a cardiac gating signal which is shifted timewise from the diastole signal. The clinical usefulness of cardiac images obtained in this manner has been discussed in the following references: King, "Stop Motion Cardiac Imaging", *Cardiac Ultrasound*, Hipona et al ed., in press; Teichholz, "Echocardiography in Coronary Artery Diseases", Ibid; and Kikuchi, "Development and Present Aspects of Ultrasono-cardio-tomography," *Ultrasonics in Medicine*, DeVlieger et al ed., American Elsevier Publications, 1974, pp. 230–238.

Computer techniques have been reported in sorting and assembling multiple images per heart cycle using recorded data from several heart cycles; Waag et al, "Processing and Display of Cardiac Ultrasound Data", *Proc. 26th Ann. Conf. on Engineering in Med. and Biol.*, 1973, p. 419; Waag, "Computerized Cine Ultrasound Cardiography", *Cardiac Ultrasound*, Hipona et al, ed., in press; Wixson et al, "Computer Acquisition and Processing of Left Ventricular Echocardiograms", *Proc. 19th Ann. Conf. of Am. Inst. of Ultrasound in Med.*, 1974 p. 46; and McSherry, "Ultrasonic Cardiac Imaging and Image Enhancement Technique", lecture paper delivered at 1974 IEEE Ultrasonics Symposium, Milwaukee, Wisconsin.

The Kikuchi article in particular provides a good backdrop for the present invention. One of the systems described in Kikuchi calls for using an oscilloscope to display the echo information from a number of cardiac cycles one at a time from the same point in each cycle. Between cycles of course the transducer beam is repositioned so that in the end the plurality of closely adjacent lines that the oscilloscope has displayed one at a time will represent a tomograph (cross-sectional slice) of the heart when photographed for cardiac examination. For illustrating motion, the Kikuchi article suggests filming photographs of successive images with a movie camera. The result is an animated simulation of the motion of the structures in view. The Kikuchi article also refers to a multiplex (multi-image) display technique in which the first image is triggered by the R-wave of the patient's ECG current and there is a preset uniform interval between each image.

SUMMARY OF THE INVENTION

The general purpose of the invention is to faciliate the production of synchronized multiple cardiac tomographic images.

According to the invention, a scan converter storage surface is divided into a plurality of image spaces (preferably nine) corresponding to different points in time within the heart cycle. In the preferred embodiment ultrasound echoes reflected by cardiac structures are plotted in the various image spaces by means of special x, y transducer sweeps indicative of the angle and position of the transducer and the velocity of propagation of sound in tissue. The transducer sweeps are offset consecutively by electronic counting circuitry to the image spaces corresponding to the selected points within the cardiac cycle. Separate delay and image spacing counters allow each line of the first image to be stored at a predetermined time following detection of the QRS complex of the patient's ECG and lines for successive images to be stored at an independently determined uniform interval. An analog trace of the filtered ECG waveform is stored at the bottom of the first image space. Bilevel cursor marks are superimposed on the filtered ECG to indicate the points within the heart cycle at which the various images are stored. The scan converter storage surface is read out by means of television (TV) sweeps to a TV display. During image build-up, the read and write modes alternate. If desired, the TV sweeps to the scan converter may be attenuated and offset to display a single stored image full screen. Images in sequence provide automatic animation. A self test circuit substitutes as internally generated fake ECG waveform and writes bars in the scan converter image spaces using the TV sweeps for the scan sweeps. The timing circuitry for the normal images, as set by the delay and spacing counters, gates the video for the bars. All of the timing for the system is preferably derived from a standard TV composite sync signal and the patient's ECG current.

BRIEF DESCRIPTION OF THE DRAWINGS

FIG. 7 is a schematic and block diagram illustrating the ECG amplify, filter and detect circuit of FIG. 2 in more detail.

FIG. 8 is a schematic circuit diagram of the peak follower detector of FIG. 7.

DESCRIPTION OF THE PREFERRED EMBODIMENTS

Figure 1:
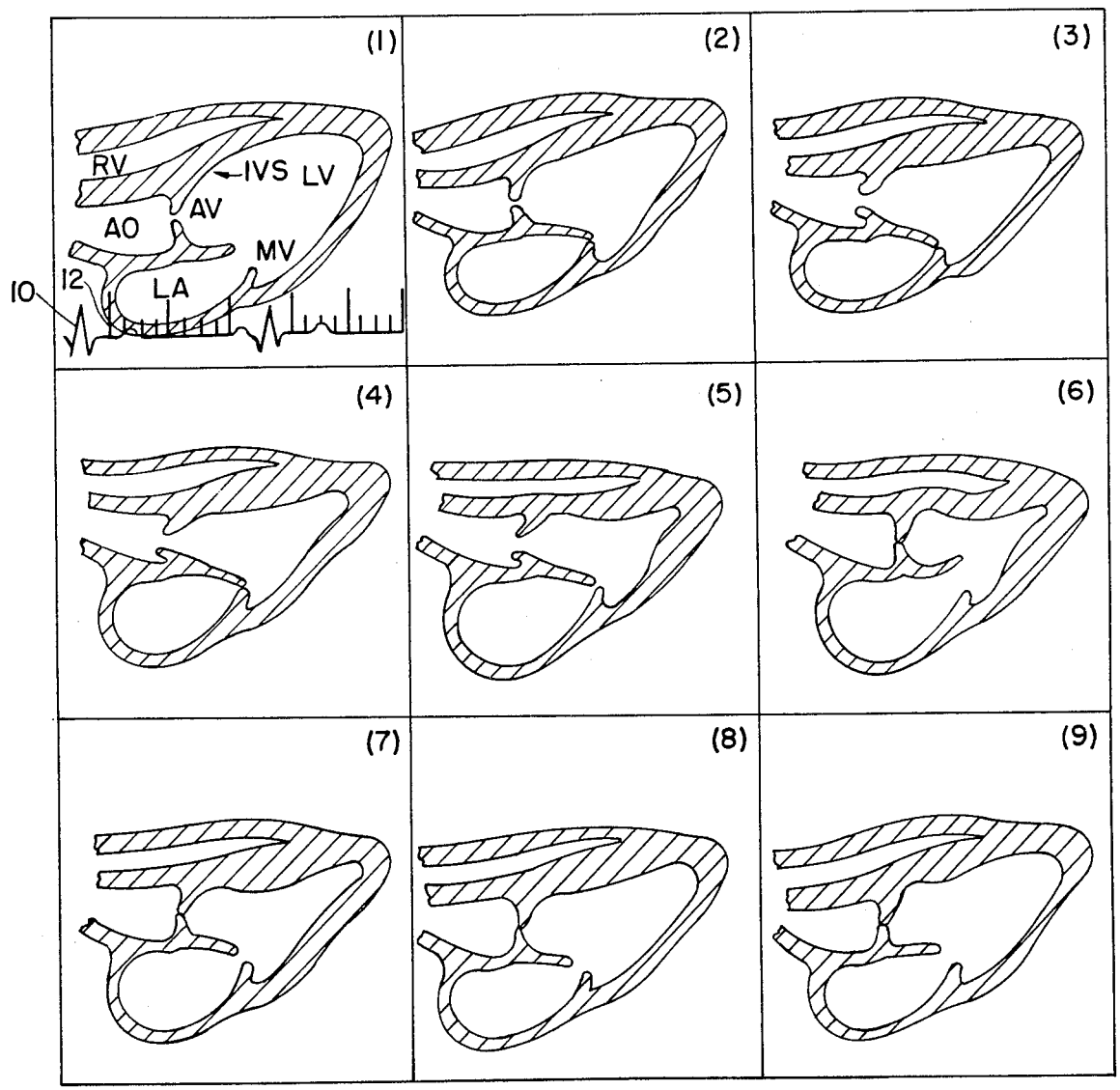
FIG. 1 is a schematic and pictorial diagram of the preferred display according to the invention illustrating nine completed images and an ECG waveform with superimposed cursors.

The apparatus described below is specifically designed to generate nine tomographic images of the heart at selected points of the cardiac cycle using multiple image gating. To provide a preview of the type of display which this apparatus achieves and an understanding of the value of the display in diagnosis, FIG. 1 shows a sketch of nine completed images, each obtained at a different successive point of the cardiac cycle. The images are numbered 1–9 from left to right and top to bottom for identification (The numbers do not appear on the display.) The orientation of the heart image is with the apex of the heart pointing to the right and chest wall at the top. The posterior heart wall is toward the bottom with the aortic root (AO) and left atrium (LA) toward the left. This projection is similar to a left interior oblique angiogram. The right and left ventricles (RV and LV), interventricular septum (IVS) and the aortic and mitral valves (AV and MV) are clearly identifiable in these sketches. Along with heart image at the bottom of the first image space, a two second trace 10 of the patient's ECG waveform is displayed with cursor marks superimposed thereon to indicate the point within the heart cycle to which each of the images corresponds. The first, fifth and ninth cursor marks are of increased amplitude for ease in identification. The first image shows the heart at the end of diastole. This is indicated by the first cursor mark 12 which comes immediately after the QRS complex of the ECG waveform 10. The QRS complex is identifiable as the largest voltage spike (R-wave) in the ECG 10 flanked by two smaller spikes of opposite polarity (Q and S).

In the first image at the end of diastole, the mitral valve is open and the left ventricle is at its largest size. Images 2 through 5 in FIG. 1 correspond to successive points in systole. This is indicated by the closed mitral valve, open aortic valve and decreasing ventricle size. Images 6–9 correspond to diastole and show increasing left ventrical volume along with a closed aortic valve and open mitral valve.

Figure 2:
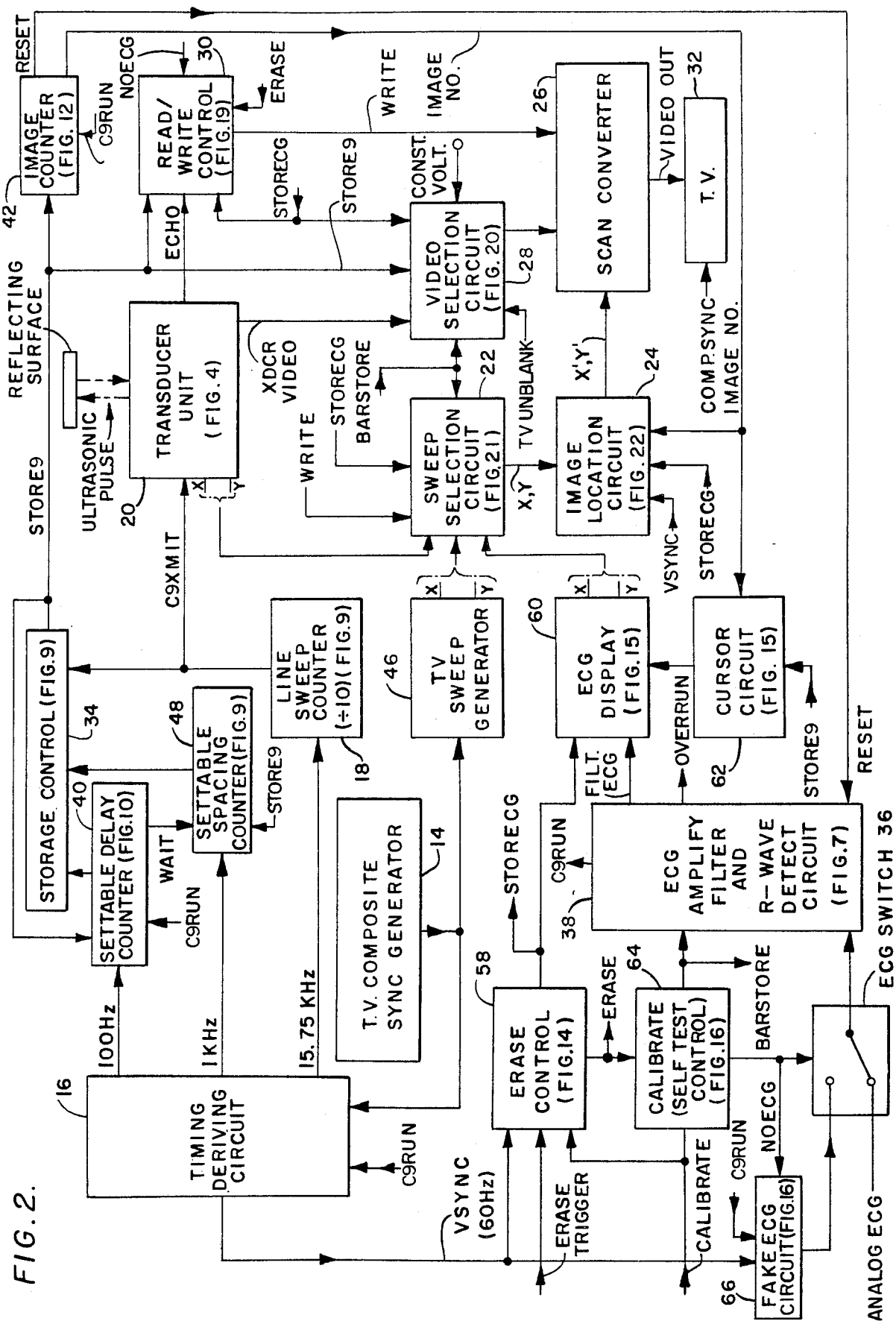
FIG. 2 is an overall functional block diagram of a preferred embodiment of the invention.

FIG. 2 provides an overview of the main functional parts of the entire system. A television composite sync generator 14 is the central timing source from which all timing signals are derived. A timing deriving circuit 16 receives the TV composite sync signal and strips off the vertical sync (VSYNC) and the horizontal or line sweep signal. The line sync signal at 15.75 kHz is internally multiplied by 4 and divided by 63 to produce an output clock of 1 kHz and divided again by 10 to produce an output clock of 100 Hz. The line sweep signal at 15.75 kHz is fed to a line sweep counter 18 which produces an output pulse every 10 lines. This output pulse is a main system binary control signal C9XMIT which orders the transducer unit 20 to transmit an ultrasonic pulse every 10th line of the line sync signal. At the same time the transducer unit 20 transmits a pulse, it generates deflection voltages X and Y which correspond to the location and orientation of the beam produced by the transducer. These signals are referred to as transducer sweeps. The transducer sweeps are passed via a sweep selection circuit 22 and an image location circuit 24 to a scan converter 26. Similarly the analog transducer video output, representing the return from reflecting surfaces, is passed from the transducer unit 20 via a video selection circuit 28 to the scan converter 26.

The scan converter 26 is an opaque cathode ray tube in which the target of the tube carries a matrix of tiny capacitors (preferably, in a 1,000 by 1,000 matrix), instead of a phosphor layer. This capacitor matrix provides the storage surface of the scan converter. Writing into the storage surface consists of controlling the direction of an electron beam to introduce a charge pattern over the capacitor matrix. Except for leakage, the capacitor array will retain the charge pattern indefinitely. For readout, the electron beam is swept over the charged capacitor matrix and the video signal is taken off a signal plate adjacent the capacitor array as in a TV camera.

The transducer unit 20 also produces an output, in conjunction with other control signals, to a read/write control 30. The control 30 tells the scan converter 26 when to write data into its storage circuit and when to read it out to a TV receiver display 32.

Although the transducer unit 20 is transmitting ultrasonic pulses and receiving reflected echoes with each C9XMIT signal, nothing is written into the scan converter storage surface until a storage control 34 produces the binary signal STORE9. This command signal plays many roles in the system. The ECG waveform is passed via ECG switch 36 to the ECG amplify, filter and detect circuit 38. When the R-wave in the live ECG of the patient is detected by the circuit 38, it produces a control signal C9RUN. This control signal starts a settable delay counter 40 which establishes the preset delay between the R-wave and the selected point in the heart cycle to which the first image will correspond.

Figure 3:
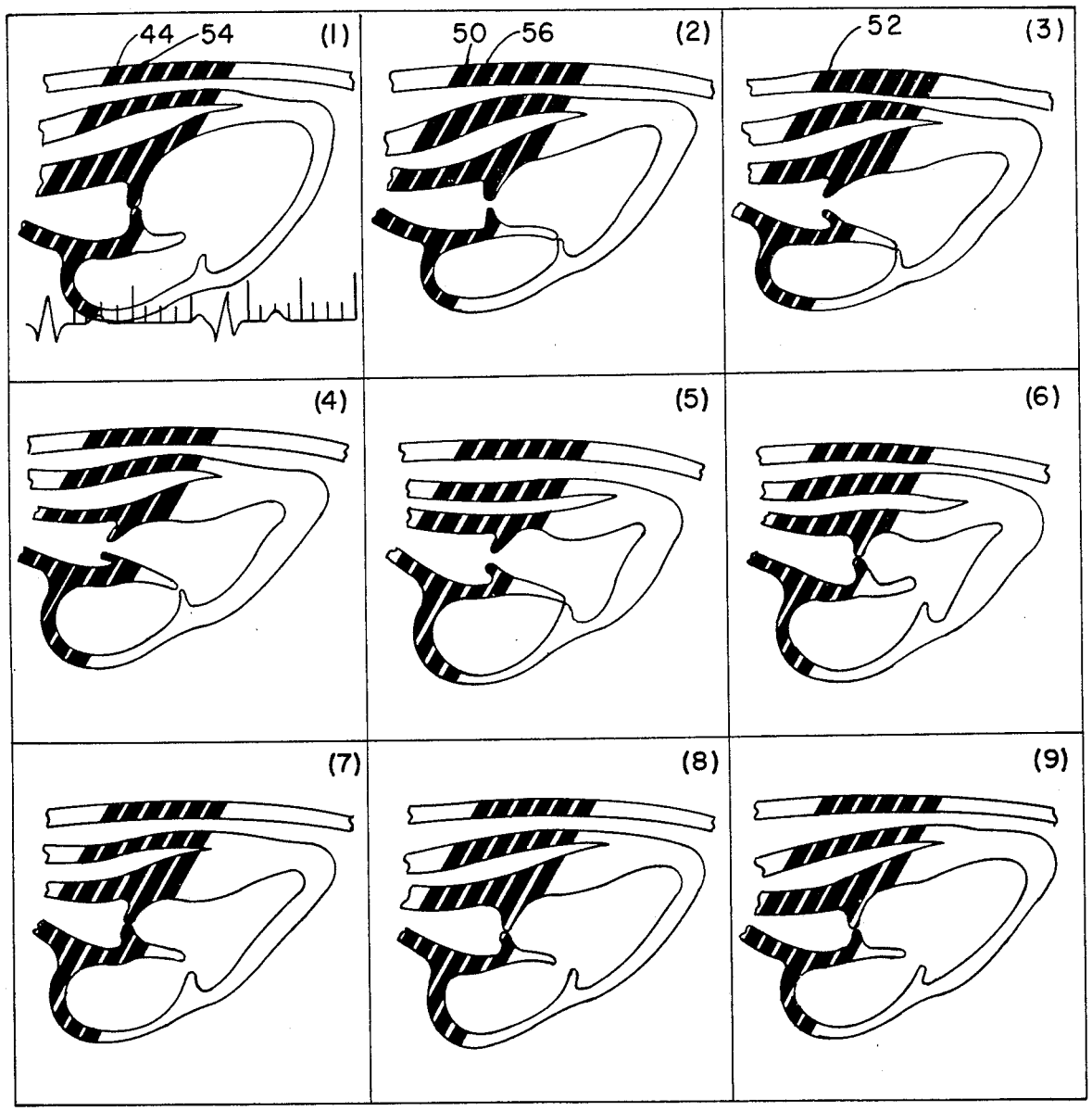
FIG. 3 is a schematic and pictorial diagram of the display according to the invention about halfway through the generation process to show the build-up of individual scan sweeps.

Receiving the 100 Hz clock signal from the timing circuit 16, the delay counter 40 counts the delay and, at the end of the delay interval, produces a control signal to the storage control 34 which responds by producing, coincident with the next C9XMIT signal, a STORE9 command signal which lasts for 20 horizontal lines. This signal enables the scan converter 26 to receive the transducer sweeps and the transducer video to write the results of one transducer pulse return into the scan converter storage surface. The first STORE9 command signal is also passed to an image counter 42 which immediately registers the first image. The image number output of the counter 42 is directed to the image location circuit 24 which causes the transducer sweeps X, Y to be attenuated and offset to the upper lefthand one ninth area of the storage surface. These sweeps are represented by X', Y'. Thus the first line of information is written on the scan converter surface. In FIG. 3 the line just described would correspond to diagonal line 44 in the first image. When the STORE 9 signal goes FALSE ("0" logic state) after twenty lines, the read/write control returns the scan converter to the read mode. The absence of the WRITE signal allows the sweep selection circuit 22 to provide TV sweeps X, Y from a TV sweep generator 46 timed by the TV composite sync generator 14, to pass to the scan converter 26 via the image location circuit 24. At this time, the image location circuit 24 does not attenuate the offset the TV sweeps but reads out all image spaces. At this instant, then the TV display 32 will show one line 44, and one line only, in the upper lefthand corner of the screen. From this point on, the read and write modes of the scan converter alternate with the absence and presence of the STORE9 command signal respectively until the images are complete. It should be noted, however, that the image accumulation process can be stopped at any time by disabling the storage process whereupon the ECHO output to the read/write control 30 changes stage causing the scan converter 26 to remain in the read mode.

For the second line, corresponding to the second image space, the settable spacing counter 48 beings counting from the time of the first STORE9 signal clocked by the 1 kHz output of the timing circuit 16. The spacing counter 48 produces an output to the storage control 34 after the selected interval has elapsed. When the C9XMIT signal occurs the STORE9 output of the storage control 34 becomes TRUE causing a second line 50 in FIG. 3 to be written as the first line of the second image. The occurrence of the second STORE 9 command signal also causes the image counter 42 to increment by one with the result that the image location circuit 24 changes the transducer sweep offset so that the second line 50 will be written in the second image space. The second STORE9 command signal also causes the spacing counter 48 to repeat its count so that the third STORE9 signal will be spaced from the second STORE9 signal by the same interval that the second was spaced from the first. Similarly, the third time that the STORE9 signal of the storage control 34 becomes TRUE, the third line 52 in FIG. 3 will be written as the first line of the third image. This process continues until each of the nine images has a first line of information about the heart. The entire process of writing the nine lines in the nine respective images takes one heart cycle. When the ninth image count is reached, the image counter 42 produces a reset control signal to the circuit 38 which makes the C9RUN signal FALSE. In turn, the delay counter 40 tells the spacing counter 48 to stop counting and wait until the next STORE9 signal occurs.

At the end of the first heart cycle, the transducer is relocated normally by hand to an adjacent orientation and/or position. This location not only changes the echo return but also changes the transducer sweeps X, Y to indicate the new location of the transducer.

When the next R-wave is detected by the circuit 38, the TRUE C9RUN signal causes the line writing process to be reiterated by resetting the delay counter 40. In the second heart cycle the first STORE9 signal causes the line 54 in FIG. 3 to be written as the second line of the first image adjacent to the original line 44. The second time the STORE9 signal becomes TRUE, a line 56 will be written in the second image space adjacent to the line 50.

The space between the lines 44 and 54 in image 1 or between lines 50 and 56 in image 2 is merely illustrative and depends on the relocation of the transducer. It is obviously perferable for all of the lines to be parallel adjacent to each other. One reason why this is not usually possible in practice is that the approach (acoustic window) to the heart ultrasonically is through the left parasternal region, particularly the fourth intercoastal space. Both ribs and lungs must be avoided. In practice there may not be enough space to keep the transducer in parallel each time. Thus the image pattern typically takes on a fan shape since it is primarily the orientation of the transducer which is being changed rather than the position, in order to stay within the designated acoustic window.

Prior to storing any of the transducer scans in the scan converter 26, the ECG with cursors can be stored in the first image space if desired by activating an ERASE TRIGGER switch which causes the erase control 58 to produce a binary control signal STORECG after insuring that the scan converter is erased. The STORECG signal is passed to an ECG display unit 60 which initiates an X-sweep, an internally generated, linear, ramp waveform. The filtered ECG is a continuous analog output of the circuit 38 to the ECG display 60. The amplitude of the filtered ECG determines the Y deflection voltage. At the same time the STORECG signal causes the video selection circuit 28 to choose a constant voltage video signal and the sweep selection 22 to choose the ECG sweeps X and Y to control deflection in the scan converter 26. Similarly, the STORECG signal causes the image location circuit 24 to offset the sweeps to the first image location. Consequently, the scan converter 26 writes a segment of the ECG waveform in the first image space. Cursor 62 adds marks to the waveform. Cursor circuit 62 causes the STORE9 signal to be summed with a binary input representing the images 1, 5 and 9 to produce a cursor signal which is summed with the filtered ECG to produce the Y deflection voltage.

A self-test circuit is included in the system of FIG. 2. When the CALIBRATE switch is activated, the erase cycle is initiated and thereafter the calibrate control 64 produces an output NO ECG which activates the ECG switch 36 to allow the circuit 38 to receive the output of the fake ECG circuit 66. The fake ECG circuit 66 takes the VSYNC signal from the timing circuit 16 and produces a 30 milisecond pulse. This digital signal is designed so that one beat will occur and the following beat will not occur until the ninth STORE9 signal has passed. The circuit 38 detects the "beat" as an R-wave and issues a TRUE C9RUN which begins the process which causes the storage control 34 to produce nine TRUE STORE9 signals in succession.

The calibrate control circuit 64 also produces an output signal BARSTORE. This signal causes the sweep selection circuit 22 to choose the TV sweeps X, Y as if it were going to read out the scan converter. However, BARSTORE is also an input to the video selection circuit 28 and the NO ECG signal (TRUE with BARSTORE) is an input to the read/write control 30. When the first STORE9 signal occurs coincident with the BARSTORE and NO ECG signals, the video circuit 28 selects constant voltage for the video input while the TV sweep X, Y are providing the deflection voltage for the scan converter 26. The STORE9 signal from the storage control 34 always remains TRUE for 20 horizontal lines. Thus the scan converter will write in the first image space, as dictated by the image location circuit 24, a horizontal stripe 20 horizontal lines in width. The vertical location of the stripe will depend on the setting of the delay counter 40. The vertical spacing of the rest of the bars and the rest of the images from the bar in the first image is determined solely by the spacing counter 48. Thus it is possible to have all the bars lined up with the right setting of the spacing counter. After the self-test is satisfactorily completed the ERASE TRIGGER switch is activated which causes the analog ECG from the patient to be stored in the first image. Thereafter, a new image building process can begin.

Figure 4:
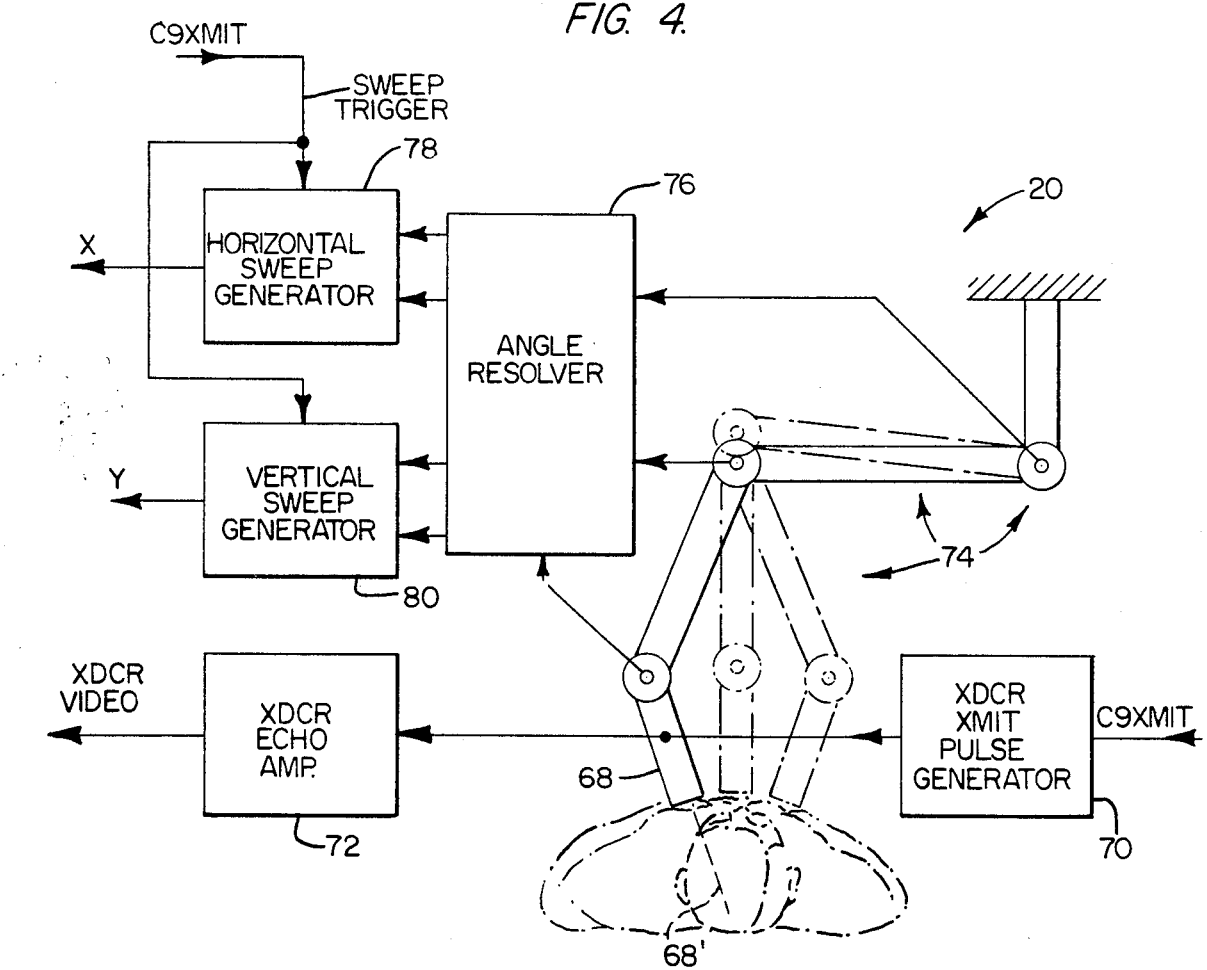
FIG. 4 is a schematic and block diagram of the transducer unit of FIG. 2 illustrating the transducer arm assembly in use on a patient and the electronics associated therewith.

As shown in FIG. 4, the transducer unit 20 of FIG. 2 includes a transducer 68, having a ceramic transducer at the end to which a coupling gel is applied before the transducer end is placed in contact with the patient's skin at the parasternal region. The axis of the elongated member containing the transducer is approximately the same axis as the beam 68' of the transducer.

The transducer 68 emits a pulse of ultrasonic energy when activated by the transducer transmit pulse generator 70 which is triggered by the C9XMIT signal from the line sweep counter 18 of FIG. 2. The echo return from a reflecting surface to the transducer 68 is passed to an echo amplifier 72 which feeds the transducer video output to the video selection circuit 28 of FIG. 2.

Figure 6:
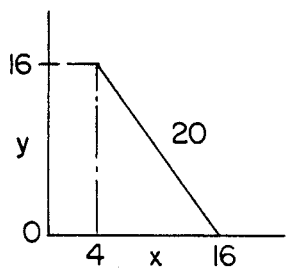
FIG. 6 is a graph of a display of a constant echo using the X, Y deflection voltages of FIG. 5.

The transducer 68 is connected to a scanner arm assembly 74, which holds the transducer in a given position established by hand and reads out, by means of rotary potentiometers at the arm segment joints, electronic values which define the angle and position of the transducer at any given point. These signal values are given to an angle resolver 76 which transforms them into Cartesan coordinates which locate the ends of a line segment (FIG. 6).

Figure 5:
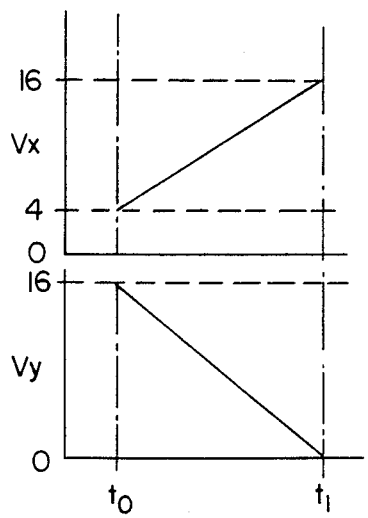
FIG. 5 is a graph of the X, Y deflection voltages from the transducer unit of FIG. 4.

The angle resolver 76 produces outputs to horizontal and vertical sweep generators 78 and 80 triggered simultaneously by the C9XMIT signal. The sweep generators 78 and 80 produce deflection voltage outputs X and Y, each of which is a linear ramp as shown in FIG. 5, that causes the electron beam of the scan converter to be swept in a staight line at a rate corresponding to the propagation velocity of ultrasound in tissue. FIG. 5 indicates values of the deflection voltages chosen, for convenience. If the beam 68' is angled approximately as shown in FIG. 4 and a Cartesan coordinate system is superimposed, let us assume that the top lefthand end of the beam is at $X = 4$ and the lower righthand end of the beam (choosing the beam length arbitrarily as 20 centimeters) is at $X = 16$. Let us also assume that the upper lefthand end of the beam 68' is at an elevation of $Y = 16$ and the lower righthand end of the beam is at $Y = 0$. The deflection voltages corresponding to these coordinates are produced by the sweep generators 78 and 80 synchronously over a time interval $t_0$ to $t_1$, where $t_1 - t_0 = 40$ cm./ $V_p$, where $V_p$ is the propagation velocity and 40 cm. is the distance of a round trip to the deepest point of the beam. The deflection voltages shown in FIG. 5 will produce a line as shown in FIG. 6 if the transducer video is constant. In practice, of course, only bright points along this line 20 will occur to indicate where echoes occured.

FIG. 7 and 8 show the details of the amplify, filter and detect circuit 38 of FIG. 2. The output of the ECG switch 36 (normal or fake ECG) is band pass filtered in amplifier 82. The filtered ECG output is used by the display circuit 60 of FIG. 2. The filtered ECG is also passed to a full wave rectifier 84 which insures that either an upright or inverted ECG will work. The rectified output is passed via a low pass filter 86 providing further wave shaping to a peak follower detector circuit 88 shown in FIG. 8.

The detector 88 in FIG. 8 includes an operational amplifier 90 with its noninverting input receiving the output of the low pass filter 86 of FIG. 7. The output of the operational amplifier 90 is fed back to the inverting input via a diode 92. A grounded RC circuit including capacitor 94 and resistors 96 and 98 is connected in parallel between the diode 92 and the inverting input of the amplifier 90. The resulting circuit serves as a peak follower with a slow decay between each QRS complex. The output will equal the positive input plus the voltage drop across the diode 92 during the rising peak of the QRS complex. Once the peak has passed, the operational amplifier 90 goes to the negative limit while the capacitor 94 slowly decays. The positive output during the QRS peak turns on a transistor (not shown) which triggers a monostable circuit 100 in FIG. 7 whose TRUE output is DETECG. The peak following characteristic and subsequent delay provides a detection threshold which is independent of the amplitude of the patient's QRS complex. It does mean, however, that a sudden change from large amplitude pulses to smaller amplitude pulses will result in no detected beats for a few seconds following the change. This occurs during self-test since the fake R-wave is so much larger than the normal R-wave. The C9RUN flip-flop 102 in FIG. 7 is set by the DETECG output and reset when the image count indicates that the ninth image has been stored.

Figure 11:
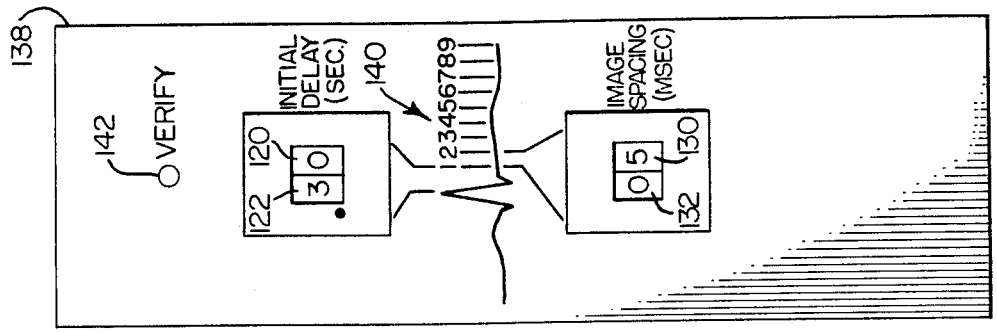
FIG. 11 is a pictorial representation of a portion of the instrument control panel with timing switches bearing a graphic indication of the relationship between delay, spacing and ECG.

The overrun D-type flip-flop 104 is clocked by the DETECG signal with C9RUN as the data input. Accordingly, if C9RUN is still TRUE when the next beat is detected (DETECG), then the overrun flip-flop 104 will be set. The overrun output of the flip-flop 104 preferably activates an indicator light on the control panel of the instrument (FIG. 11).

Figure 9:
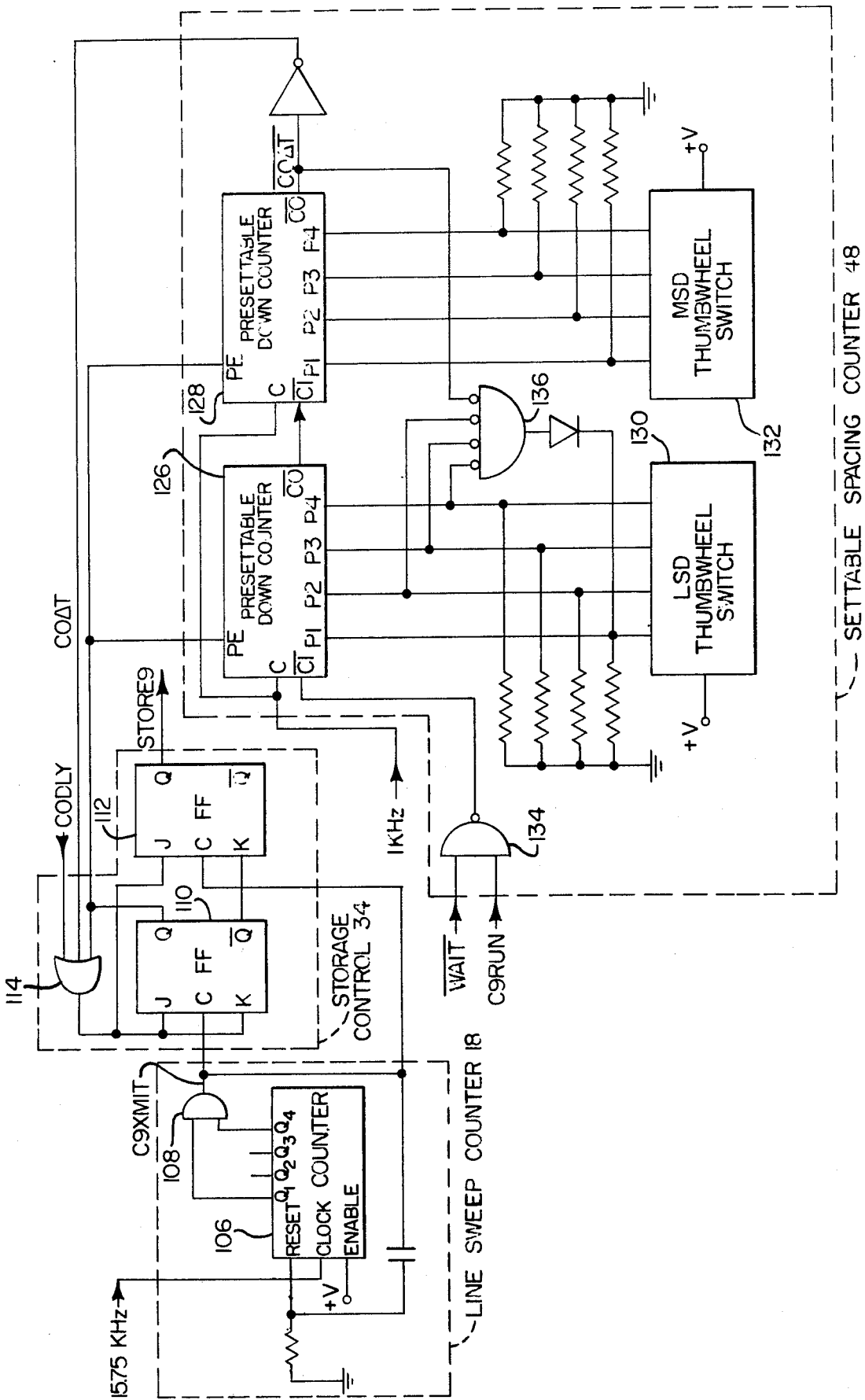
FIG. 9 is a schematic and block diagram illustrating the line sweep counter, storage control and settable spacing counter of FIG. 2 in more detail.

As shown in FIG. 9, the line sweep counter 18 of FIG. 2 includes a binary counter 106 clocked by the line sync signal from the timing circuit 16 of FIG. 2. Counter 106 is always enabled by +V level. (+V is a logic "1" level and ground is "0"). A two-input AND gate 108 receives the most and least significant output bits Q1 and Q4 which both become 1 when the count reaches 9 (1001). The command signal C9MIT is the output of the AND gate 106 which resets the counter 106 to zero. C9XMIT is thus obtained by dividing the 15.75 kHz line sync by 10. C9XMIT is TRUE for one period of the line sync signal or 63.5 usec.

The storage control circuit 34 has two J-K flip-flops 110 and 112 clocked by C9XMIT. The J, K inputs of the flip-flop 110 are tied to the output of an OR gate 114 which receives the outputs of the delay and spacing counters 40 and 48 and the fedback Q output of the first flip-flop 110. The Q input of the second flip-flop 112 is STORE9, which is TRUE for two transmit periods. The image count in image counter 42 of FIG. 2 is incremented each time STORE9 goes TRUE as discussed above.

Figure 10:
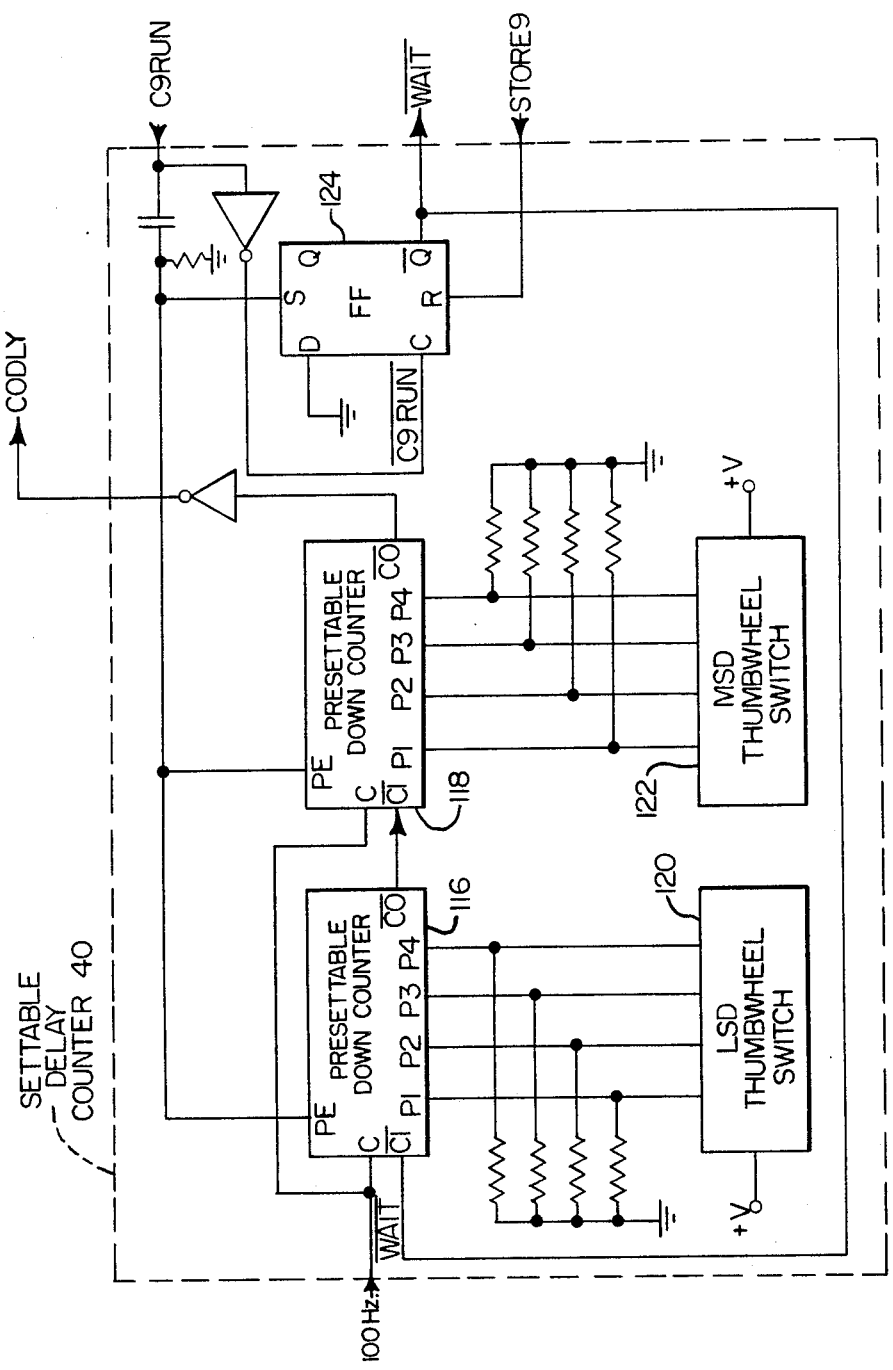
FIG. 10 is a schematic and block diagram illustrating the settable delay counter of FIG. 2 in more detail.

The settable delay counter 40 of FIG. 2, shown in detail in FIG. 10, includes two identical presettable down counters 116 and 118 having their input terminals connected as illustrated to thumbwheel switches 120 and 122 for the least and most significant digits. The counters 116 and 118 are clocked by the 100 Hz signal from the timing circuit 16 of FIG. 2. The counters are loaded with their preset count by applying a differentiated C9RUN signal to the preset enable (PE) inputs of the counters 116 and 118. The same signal sets the WAIT flip-flop 120 such that its $\overline{Q}$ ($\overline{WAIT}$) output becomes false which activates the carry-in (CI) input of the first counter 116 to begin the delay count. After the interval established by the switches 120 and 122 has been counted, the CODLY (inverted output of the second counter 118) becomes TRUE. As shown in FIG. 9, CODLY initiates a STORE9 signal. In FIG. 10 the STORE9 signal resets the WAIT flip-flop 120 so that $\overline{WAIT}$ becomes TRUE.

The spacing counter 48 shown in FIG. 9, includes a similar pair of presettable down counters 126 and 128 set by means of switches 130 and 132 as shown. Counters 126 and 128 are clocked by the 1 kHz signal from the timing circuit 16 of FIG. 2. When $\overline{WAIT}$ is TRUE, the carry-in input to the first counter 126 is enabled. When Q of the flip-flop 110 of the storage control 34 becomes TRUE, the counters 126 and 128 are loaded. The Q output of the flip-flop 110 remains TRUE for one transmit period to minimize the possibility of a 1kHz clock pulse happening at the same time. When enabled, the 1kHz clock causes the counters 126 and 128 to decrease by one at 1 msec. intervals until they reach zero. When they both reach zero, $\overline{CO\Delta T}$ goes FALSE and sets STORE9 in the storage control 32 to a TRUE level with the next occuring C9XMIT pulse. When STORE9 goes TRUE, the counters are reloaded with the values set up by the switches 130 and 132 causing $\overline{CO\Delta T}$ to go TRUE. The counters are inhibited if either WAIT is TRUE or C9RUN is FALSE by means of the NAND gate 134. If zero is set up on the thumbwheel switches 130 and 132, it is detected by the NOR gate 136 and the least significant bit of the input is pulled TRUE to result in an effective input of 1 msec.

FIG. 11 shows a portion of the control panel 138 where the thumbwheel switches 120, 122, 130 and 132 are located. Because the delay counter 40 is operated by the 100 Hz clock, thumbwheel switches 120 and 122 read out directly in 100ths of a second. Likewise, because the 1 kHz clock is used for the spacing counter 48, the thumbwheel switches 130 and 132 read out in milliseconds. A representation 140 of an ECG waveform is located between the delay and spacing switches. Cursors 1–9 are marked alongside the ECG curve. The space between the R-wave and first cursor is bracketed to the delay switches; the space between the first and second cursors is bracketed to the spacing switches. A verify light 142 operated by the overrun flip-flop 104 of FIG. 7 is also located on the control panel 138.

Figure 12:
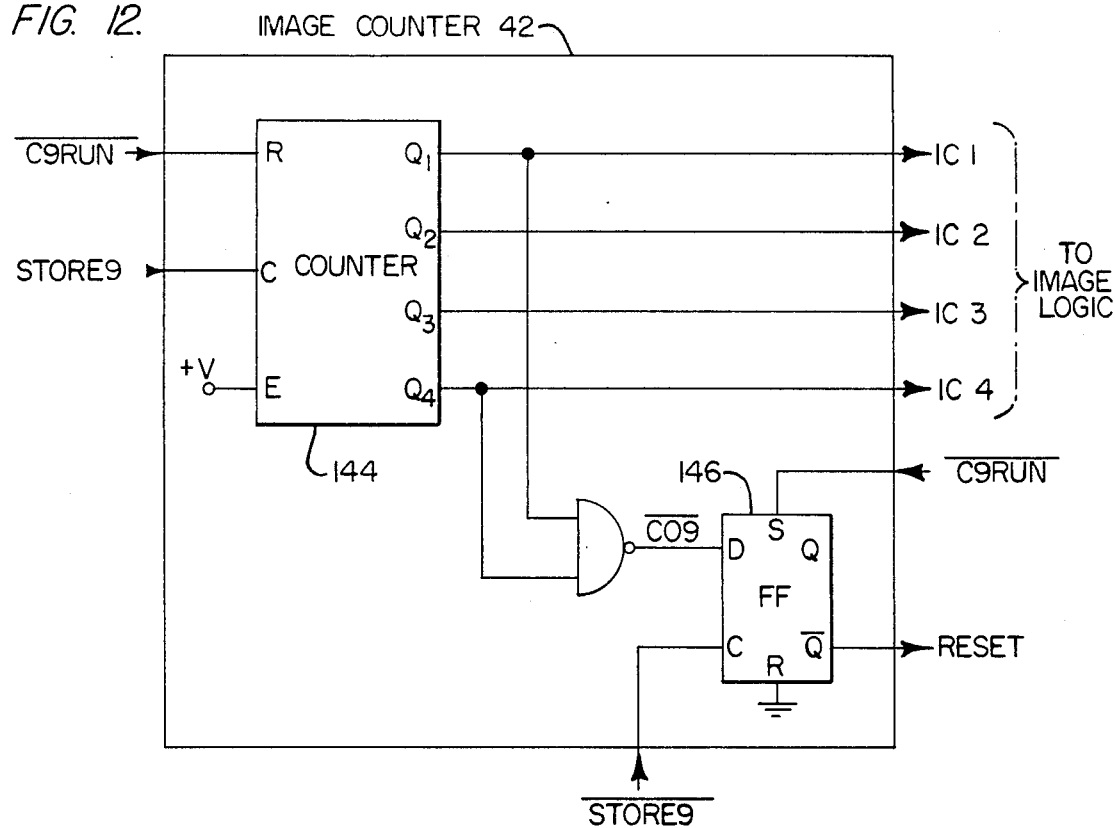
FIG. 12 is a block diagram illustrating the image counter of FIG. 2 in more detail.
Figure 13:
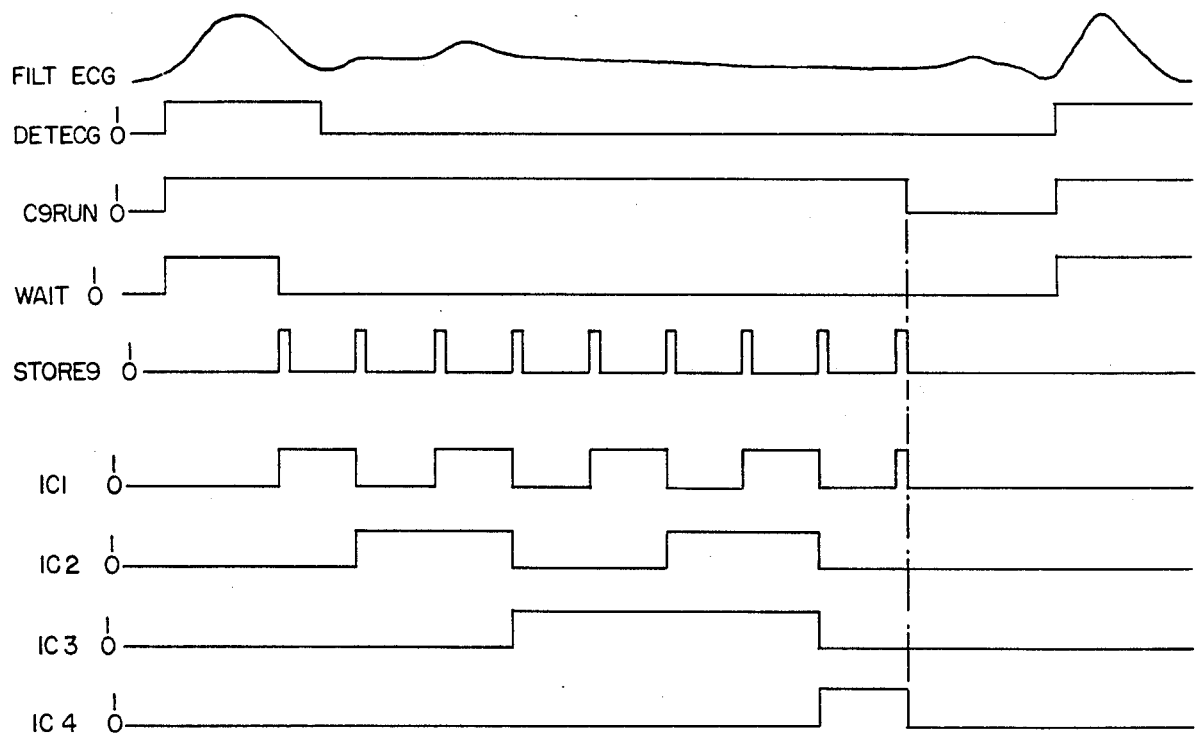
FIG. 13 is a timing diagram of major control signals generated by the apparatus of FIG. 2–12.

In FIG. 12 the image counter 42 includes a counter 144 held at zero while C9RUN is FALSE. The first STORE9 pulse after C9RUN is set causes the counter to increment to 1. Each subsequent STORE9 pulse increments the counter. When the counter reaches 9, $\overline{C09}$ goes FALSE and the TRUE-to-FALSE edge of STORE9 causes the RESET output of D flip-flop 146 to go TRUE. This terminates storage until the next R-wave by resetting C9RUN in flip-flop 102 of FIG. 7 (circuit 38). The outputs of the counter 144, IC1 to IC4, represent the four bits necessary to count from 0–9. The relationship between the image count signals and the other major signals resulting from the above described circuitry is shown in the timing diagram in FIG. 13.

Figure 14:
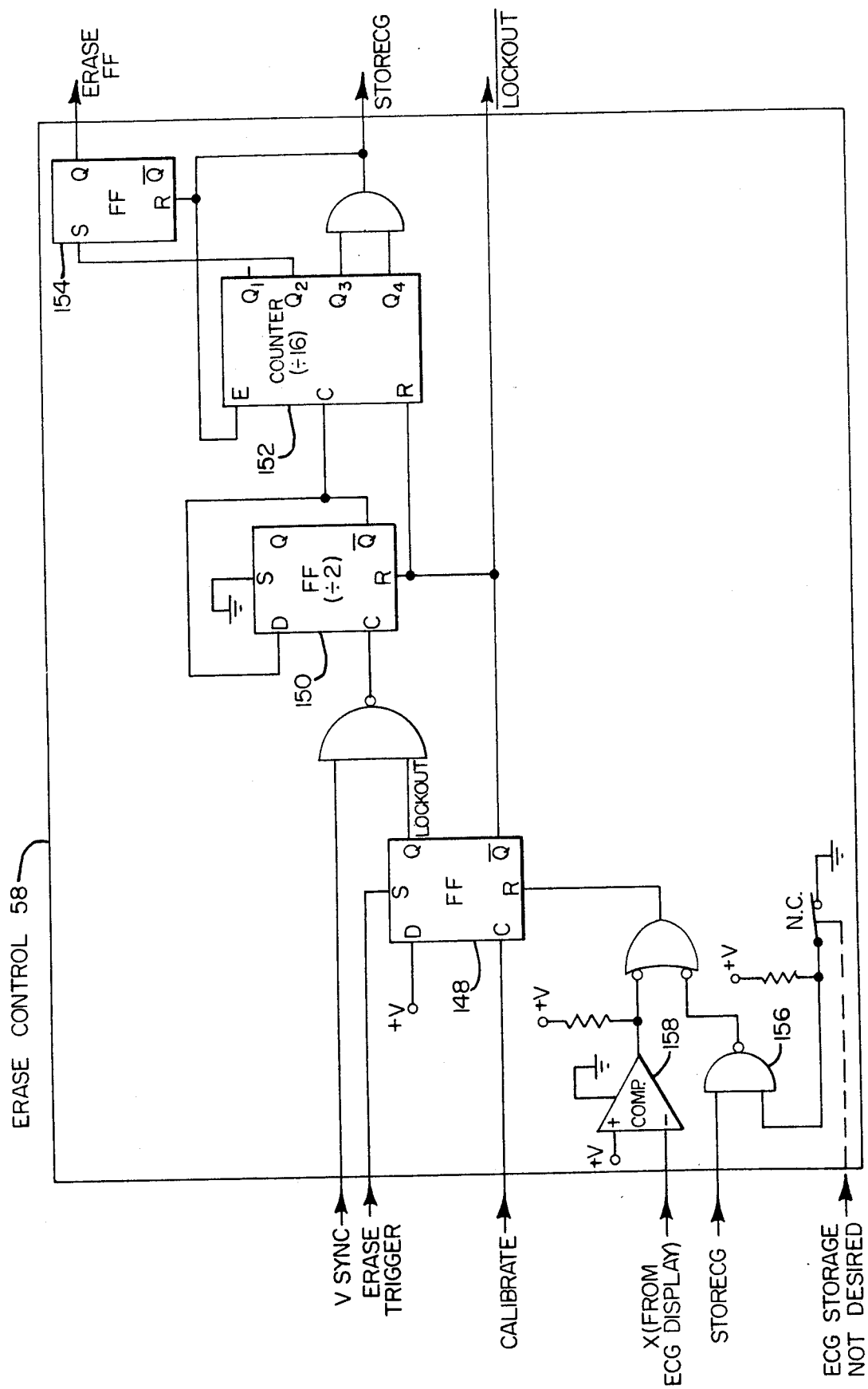
FIG. 14 is a schematic and block diagram illustrating the erase control of FIG. 2 in more detail.

In the erase control 58, shown in FIG. 14, when ERASE TRIGGER or CALIBRATE goes TRUE an erase cycle is initiated which lasts for 20 television frames (0.33 sec.). A D flip-flop 148, with its D input always TRUE, is gated by the CALIBRATE switch or set by ERASE TRIGGER to provide a LOCKOUT output (Q) which is gated by VSYNC to the clock input of another D flip-flop 150 which divides the frequency of the VSYNC signal by two to furnish the clock input to a binary counter 152. The erase flip-flop 154 is set when the counter 152 reaches 2 (0010). This ensures that the erase cycle is synchronized to VSYNC. Note that erase does not affect C9RUN. When the counter 152 reaches 12 (1100), STOREECG (Q3.Q4) goes TRUE to halt the counter and reset the erase flip-flop 154 which has now been "on" for 20 television frames, thus terminating the erase cycle.

Indicating that no ECG storage is desired immediately resets the flip-flop 148 which resets the divide by two flip-flop 150 and the counter 152 and STORECG goes FALSE. If ECG storage is desired, the reset path through gate 156 is inhibited and thus LOCKOUT remains TRUE as does STOREECG. When the ECG storage is completed, the LOCKOUT flip-flop 148 is reset by comparator 158 which senses that the time base X-sweep for the ECG display (described below) has achieved maximum deflection.

Figure 15:
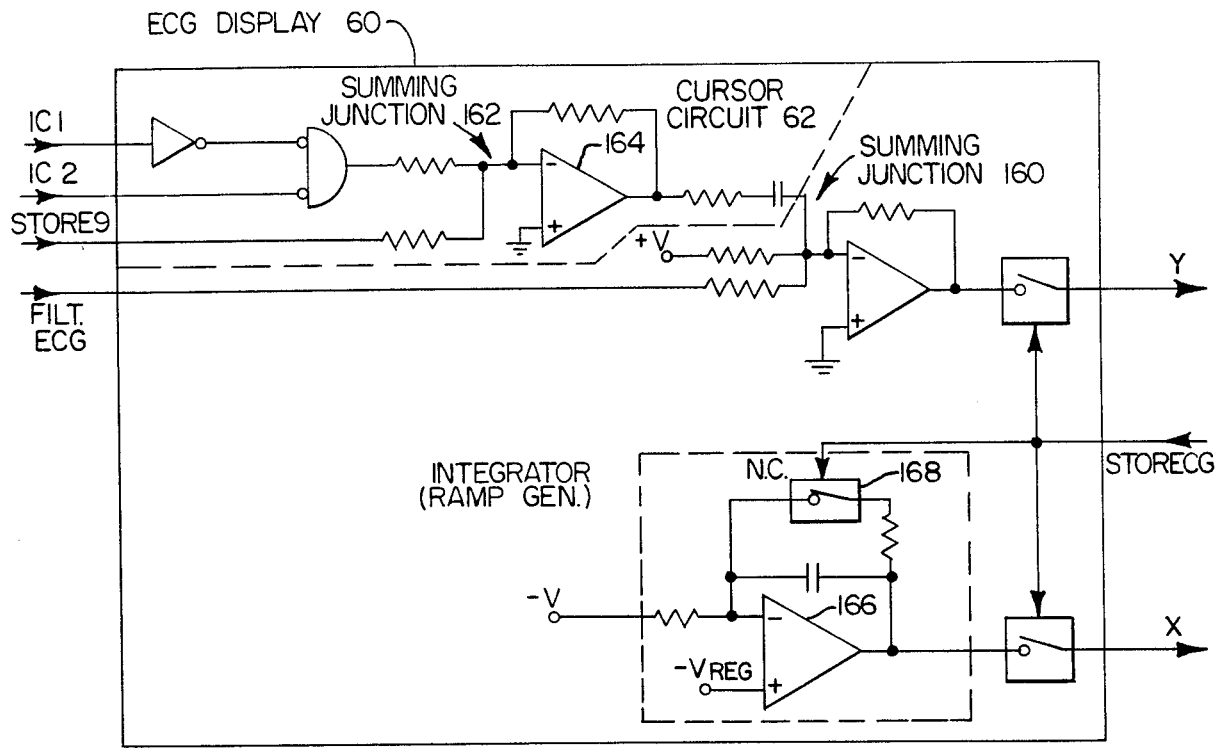
FIG. 15 is a schematic and block diagram illustrating the ECG display circuit of FIG. 2 in more detail.

The display of the ECG with cursor marks requires that a special Y-sweep be generated. As shown in FIG. 15, the filter ECG is summed with the cursors by a summing junction 160 preceding an operational amplifier 164. Cursors are produced by the STORE9 signal. Images 1, 5 and 9 are detected by IC1 being TRUE and IC2 being FALSE (see FIG. 13). For these three images a double amplitude pulse is obtained. Thus the output of the subsequent operational amplifier 164 is a series of nine rectangular pulses with the first, fifth and ninth being augmented. These pulses are differentiated and then added to the analog ECG along with a D.C. bias to produce the desired Y signal for the vertical deflection voltage.

For horizontal sweep, when STORECG goes TRUE, a ramp is generated by operational amplifier 166. The output of amplifier 166 is held at −5 volts by means of switch 168 as long as STORECG is FALSE. When the switch 168 opens, the amplifier 166 integrates from −5 volts to +5 volts in about 2 seconds. When it reaches +5 (+±5 being the excursion of the horizontal deflection voltage for the scan converter), the comparator 158 in FIG. 14 triggers and resets the LOCKOUT flip-flop 148 and thus STORECG to terminate the ECG display phase.

Figure 16:
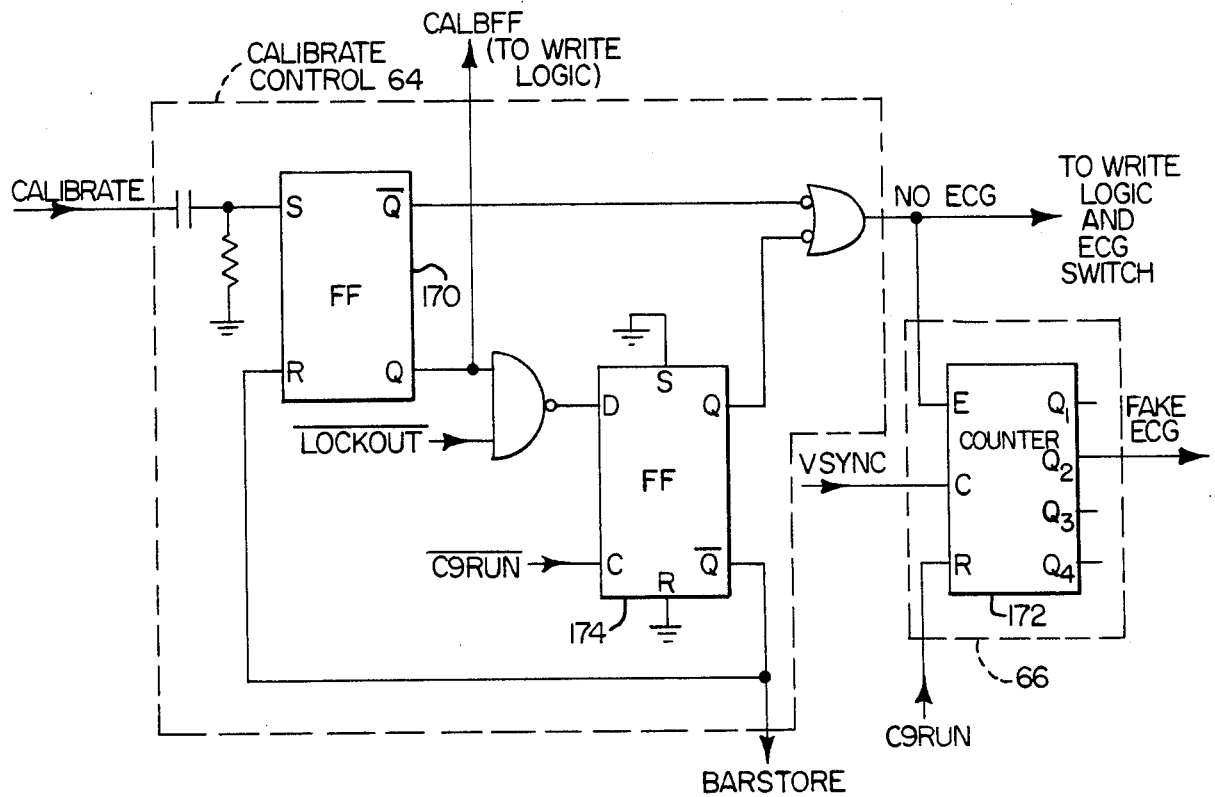
FIG. 16 is a schematic and block diagram illustrating the calibrate (self-test) control and fake ECG circuits of FIG. 2 in more detail.

Activating the CALIBRATE switch in FIG. 2 initiates a normal erase cycle by setting the LOCKOUT flip-flop 148 in FIG. 14. It also sets the calibrate flip-flop 170 in FIG. 16 to remember that CALIBRATE initiated the erase cycle. The normal erase cycle is followed by the ECG storage cycle if desired. Since CALBFF is TRUE, NO ECG is also TRUE and hence the normal ECG is replaced by means of the fake ECG counter 172, which uses VSYNC as a clock enabled by NO ECG. Using the second least significant bit (Q2) yields a 20 msec. pulse which is ample to trigger the detection circuitry as if it were an R-wave. As soon as the fake beat is detected, C9RUN goes TRUE resetting the counter 172. The counter remains reset for nine STORE9 pulses. As soon as C9RUN goes FALSE, the counter 172 starts to count another beat. Since the counter cannot operate unless C9RUN is FALSE, there will never be a premature beat generated by the fake ECG regardless of the timing selected. The number of beats stored with cursors during the two second ECG storage cycle is determined by the delay and spacing counters 40 and 48 since the new beat starts only when the timing is completed.

Figure 17:
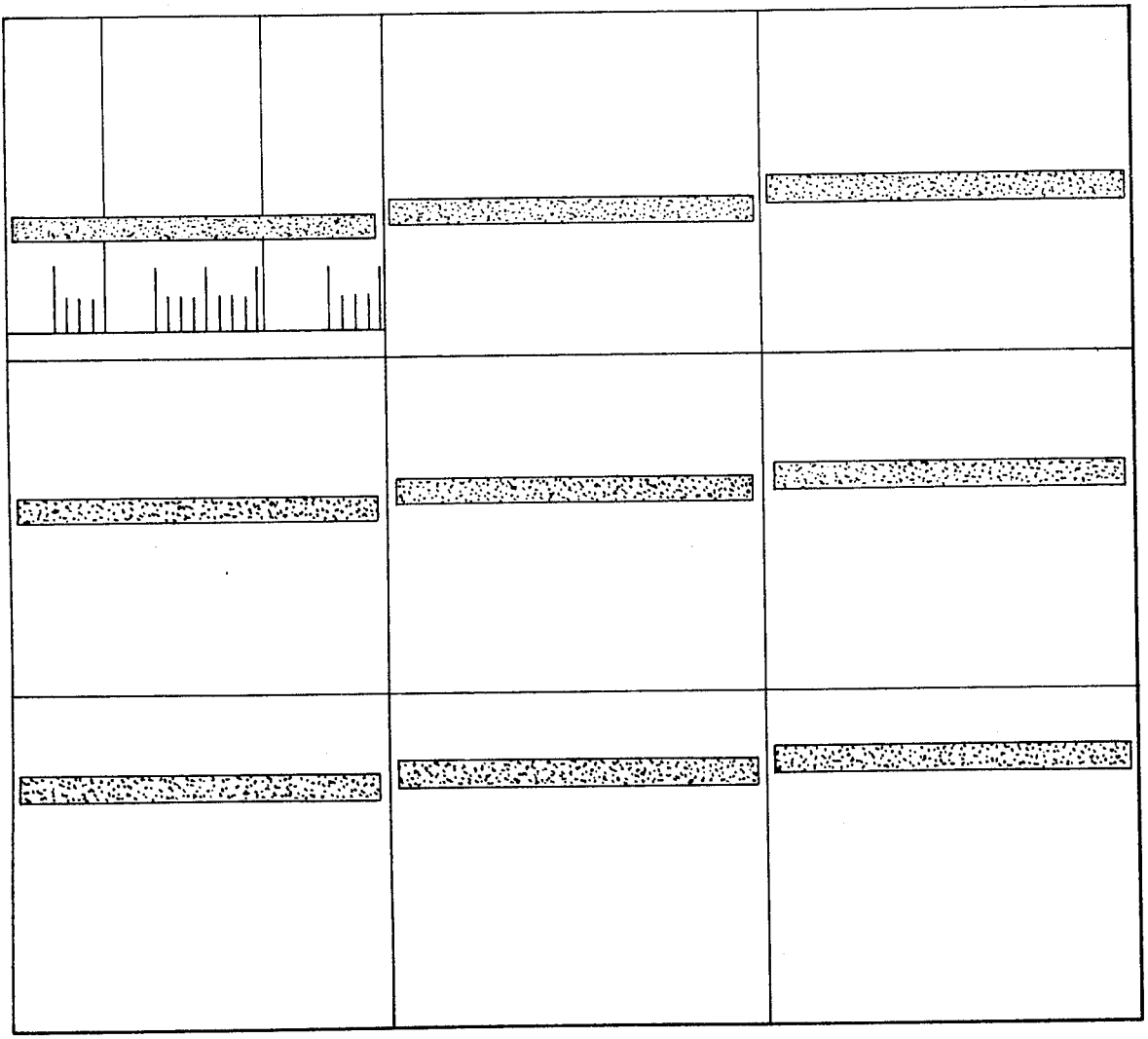
FIG. 17 is a schematic and pictorial diagram of the display during self-test procedure.
Figure 18:
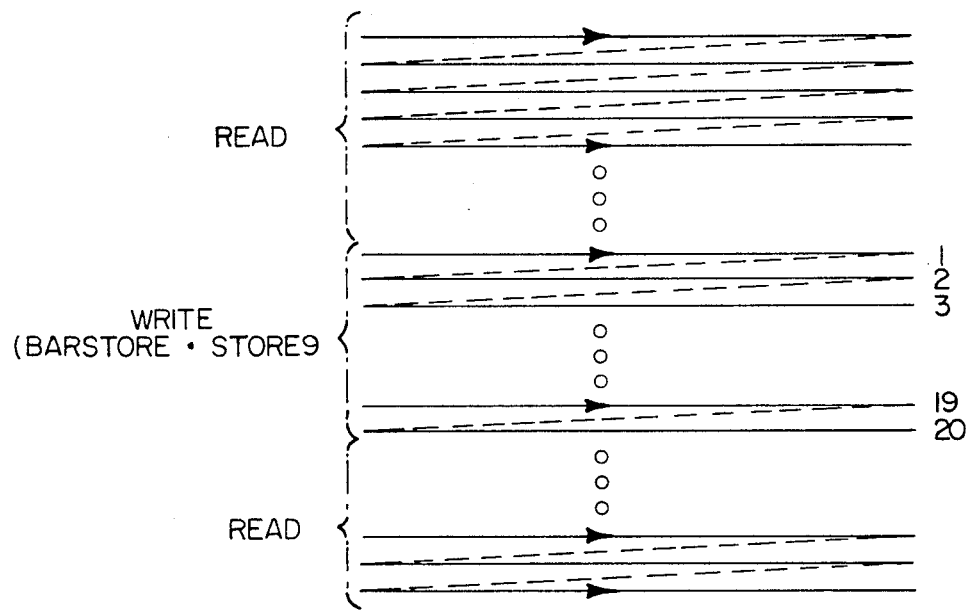
FIG. 18 is a schematic and pictorial diagram illustrating conceptually the relationship between line sweep and barstore self test.
Figure 19:
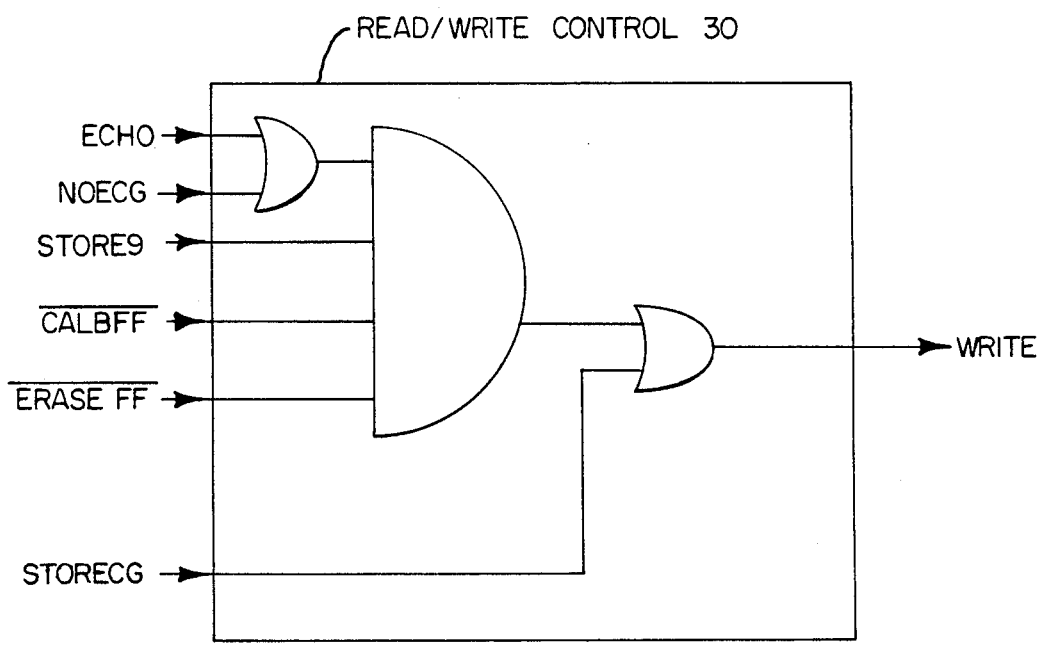
FIG. 19 is a logic diagram of the read/write control of FIG. 2.

Once the fake ECG storage is completed, the LOCKOUT flip-flop 148 in FIG. 14 is reset. This caauses the BARSTORE output of flip-flop 174 in FIG. 16 to go TRUE when C9RUN goes FALSE. CALBFF is reset when BARSTORE is set but NO ECG remains TRUE. One last fake ECG beat is generated, again synchronized by VSYNC. This last beat initiates a normal timing cycle for updating nine images. The BARSTORE signal causes the sweep selection circuit 22 in FIG. 2 to choose TV sweeps instead of transducer sweeps. The BARSTORE signal also causes the video input to the scan converter 26 to be held at constant voltage. This combination of signals results in one horizontal bar written in each of the nine image locations as indicated in FIG. 17 and 18. When all nine bars have been written, BARSTORE is reset by C9RUN bar since CALBFF is now FALSE. This completes the self-test phase.

Figure 20:
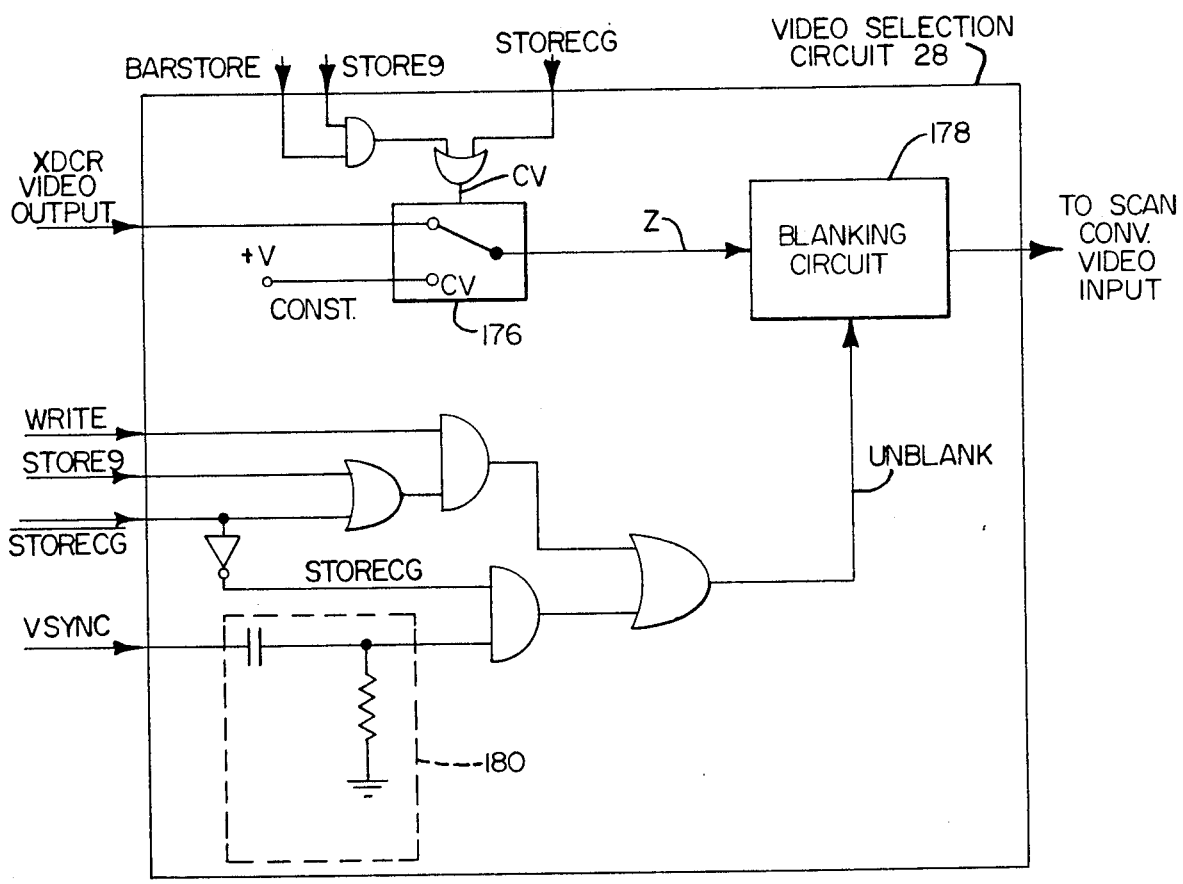
FIG. 20 is a schematic and block diagram illustrating the video selection circuit of FIG. 2 in more detail.

The logic for the read/write control 30 of FIG. 2 is shown in FIG. 20. The WRITE output of the control 30 when TRUE, causes the scan converter 26 to be placed in the write mode to write information into the storage surface represented by the X, Y sweep input and the video input. When the WRITE control signal if FALSE, the scan converter is in the read mode. According to the logic diagram WRITE is TRUE whenever STORECG is TRUE, thus enabling the scan converter to write the filtered or fake ECG in the first image space. WRITE can also be TRUE when CALBFF and ERASEFF are FALSE and either ECHO or NOECG is TRUE at the time a STORE9 signal goes TRUE. The ECHO control signal from the transducer unit 20 indicates that the transducer is producing data. The ECHO signal can be activated by a simple foot switch once the operator has established a new position for the transducer. The combination of the logic signals STORE9 and ECHO corresponds to a command for the scan converter to write a line of transducer data using the transducer video output and the transducer scans. On the other hand, the combination of the logic signals STORE9 and NOECG refers to the condition for writing bars in each image during the self-test phase.

The video selection circuit 28, shown in FIG. 20, has two purposes: to choose between the transducer video output and the constant voltage video and to control the blanking of the video signal. The transducer video aand constant voltage video are connected via an electronic switch 176 and a blanking circuit 178 to the scan converter video input. The electronic switch 176 is operated by logic gates as shown in FIG. 20 which substitute constant voltage for the transducer video whenever STORECG is TRUE or BARSTORE and STORE9 coincide.

The blanking circuit 178 is operated by logic gates as shown in FIG. 20. These gates cause the UNBLANK signal to go TRUE if WRITE is TRUE when STORE9 goes TRUE in order to unblank the video for writing transducer scans or during the self-test procedure.

A special measure has to be taken during storage of the ECG trace. The sweeps are so slow during this function that the ECG image is written too hard if UNBLANK is held TRUE. To solve this problem, a chopped UNBLANK signal is generated by differentiating the 1 kHz signal in circuit 180 of FIG. 20 to obtain a sequence of pulses a few microseconds in duration at 1 msec. intervals. These pulses are then gated with STORECG to control the UNBLANK signal. The cursors, however, would not show if UNBLANK were always chopped; thus UNBLANK is held TRUE while STORE9 is TRUE (which coincides with the cursor marks). If STORECG is FALSE, then UNBLANK is identical to WRITE.

During TV read, UNBLANK is generated either by circuitry in the scan converter 26 or in the TV sweep generator 46 in response to the TV composite sync to blank the video output of the scan converter during horizontal and vertical retrace just at the video is blanked in a television camera. When writing bars with the TV sweeps in the self-test mode blanking the video input to the scan converter during flyback is not necessary.

Figure 21:
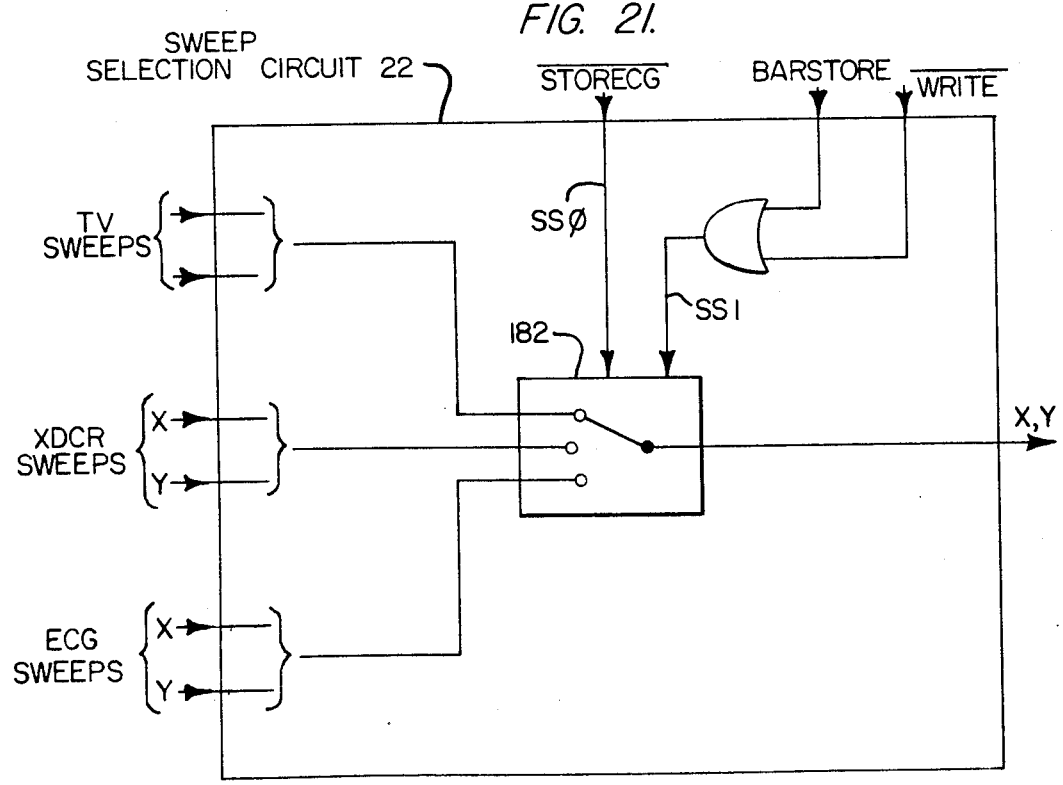
FIG. 21 is a schematic and block diagram illustrating the sweep selection circuit of FIG. 2 in more detail.

The sweep selection circuit 22 is shown in conceptual logic form in FIG. 21. A three position electronic switch 182 receives control signals SS0 and SS1: SS0 = $\overline{STORECG}$; SS1 = BARSTORE · $\overline{WRITE}$. TV, transducer, or ECG sweeps will be passed on to the scan converter 26 in accordance with the following truth table:

|      | SS0 | SS1 |
| ---- | --- | --- |
| TV   | 1   | 1   |
| XDCR | 1   | 0   |
| ECG  | 0   | 0   |

Figure 22:
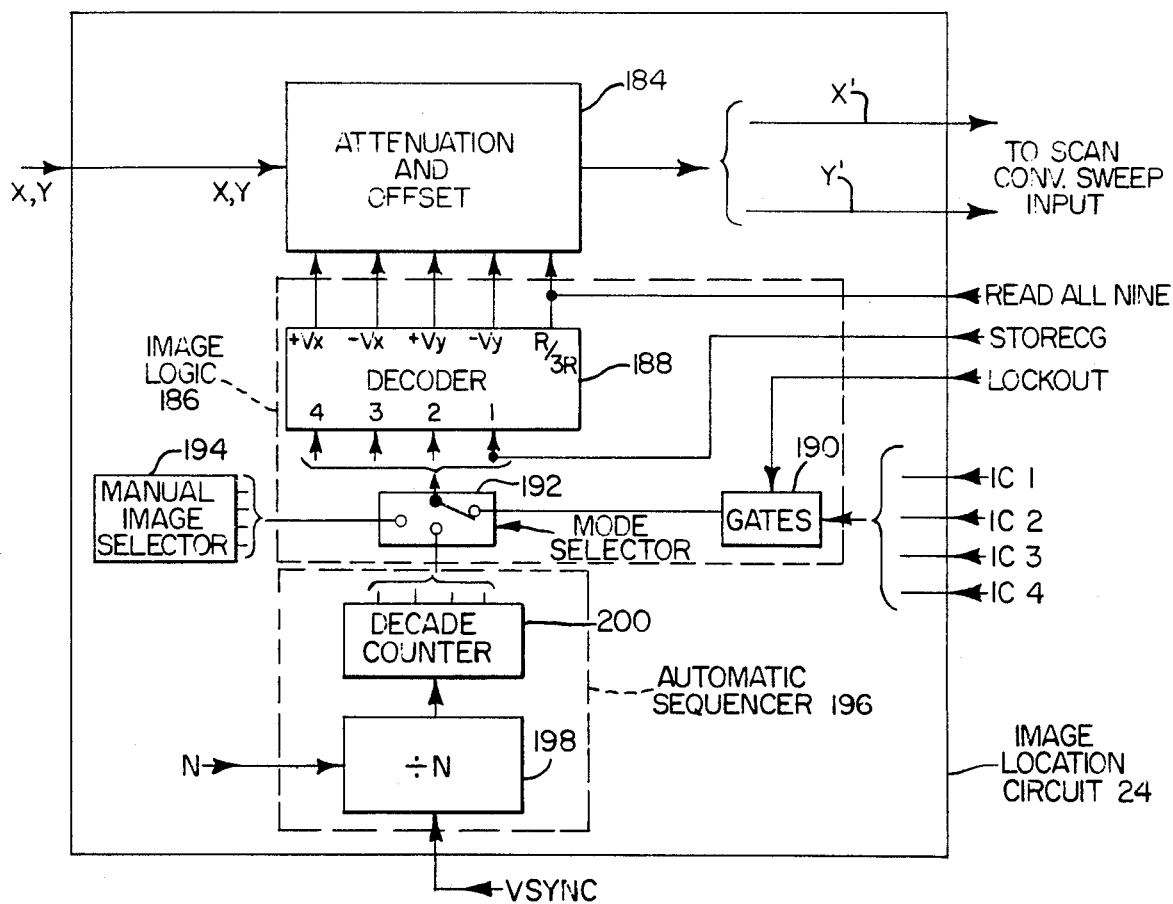
FIG. 22 is a schematic and block diagram illustrating the image location circuit of FIG. 2 in more detail.
Figure 23:
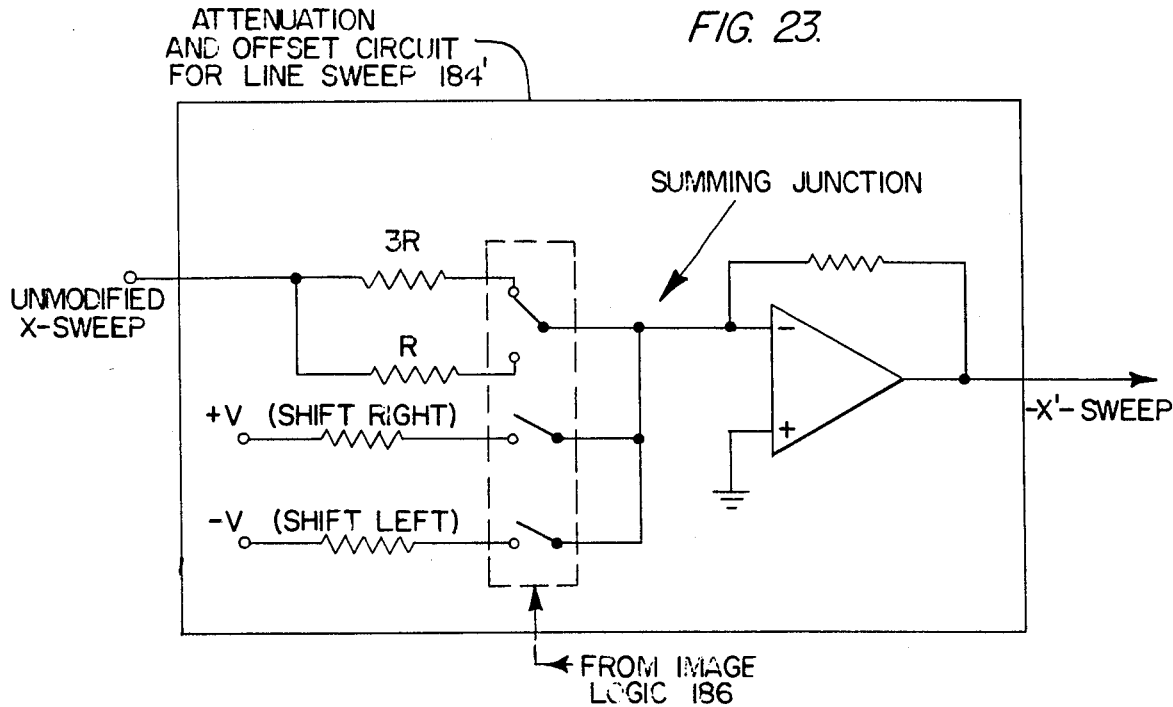
FIG. 23 is a schematic diagram illustrating one of the attenuation and offset circuits of FIG. 22 in more detail.

The image location circuit 24 of FIG. 2 is shown in FIGS. 22 and 23. The sweep signals chosen by the sweep selection circuit 22 are passed via attenuation and offset circuit 184 to the scan converter sweep input. The circuit 184 contains two substantially duplicate circuits for modifying the horizontal and vertical deflection sweeps, respectively. One of these circuits 184', the one for modifying the line sweep, is shown in schematic form in FIG. 23. The unmodified X-sweep from the sweep selection circuit 22 is passed to an analog summing circuit using standard operational amplifier techniques. Alternate resistors R and 3R (three times the resistance of R) are selected in series with the unmodified X-sweep to provide either attenuation to full screen size by inserting R or to ⅓ size by inserting 3R. Positive and negative D.C. offsets are connectible in parallel with the attenuated x-sweep. Thus it takes three bits to determine the attenuation and offset for the X-sweep as shown in the following truth table:

| Picture | 3R/$_R$ | +V | −V |
|---|---|---|---|
| Left | 1 | 0 | 1 |
| Middle | 1 | 0 | 0 |
| Right | 1 | 1 | 0 |
| Full | 0 | 0 | 0 |

When horizontal deflection voltage is ⅓ full screen size, leaving both the D.C. offset switches open ("0") leaves the X-sweep in the middle of the scan converter storage surface. Adding the positive D.C. offset, shifts the X-sweep to the right ⅓ of the screen, and to the left for the negative D.C. offset. There is another circuit identical to this one for the Y-sweep. However, attenuation factor for the vertical and horizontal sweeps may be considered identical. That is, whenever the X-sweep is reduced to ⅓ the Y-sweep will also be reduced to ⅓.

In FIG. 22 an image logic circuit 186 provides the control signals to the attenuation and offset circuit 184 to determine the location where an image is to be written or the location from which an image is to be read out. A decoder 188 accepts a four bit input to identify one of the nine possible images. These four bits can be provided from any one of four different sources. In the write mode, one of the sources of the four bit word defining the image number is from the image counter 42 of FIGS. 2 and 12. This code is passed via gate 190 and a mode selector switch 192 to the inputs of the decoder 188. To write the ECG trace in the first image space the image count input is disabled by the LOCKOUT signal to gates 190. When STORECG goes TRUE, it pulls the least significant bit input of the decoder 188 TRUE to indicate that the sweeps should be set up for the first image space. In the read mode the four bit code can be provided to the mode selector 192 by means of a manual image selector switch 194. It is important to realize, however, that although the scan converter storage surface is being read out with attenuated sweeps covering only one ninth of the area of the storage surface, the resulting video output signal to the television screen is applied over the full screen because the TV sweeps for the television are not attenuated. Rather, they are provided by an independent TV sweep generator clocked by the same composite sync signal. Thus if the manual image selector 194 selects image 3 out of the nine possible images, the third image will appear full screen on the TV display.

Another readout mode is provided by an automatic sequencer circuit 196. The VSYNC frame sweep signal is passed to a divide by N counter 198 whose output is fed to a decade counter 200 producing a four bit output to the decoder 188 via the selector 192. When automatic sequence is selected, each image is viewed in sequence on the TV display for N frames. N is determined by a switch on the control panel determining the divisor in the dividing circuit 198. By determining the number of frames per image, the rate of the sequence can be controlled to provide slow or fast animation. The bars during the self-test procedure (FIG. 17) can also be sequenced in this manner.

Figure 24:
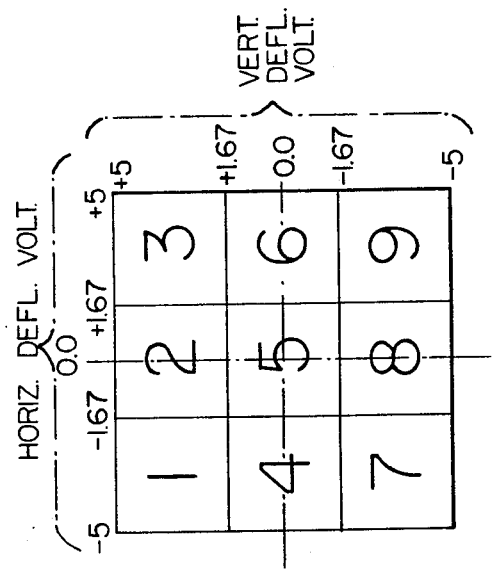
FIG. 24 is a schematic diagram of a display screen divided into nine images and indicating horizontal and vertical deflection voltage ranges for each one of the images.
Figure 25:
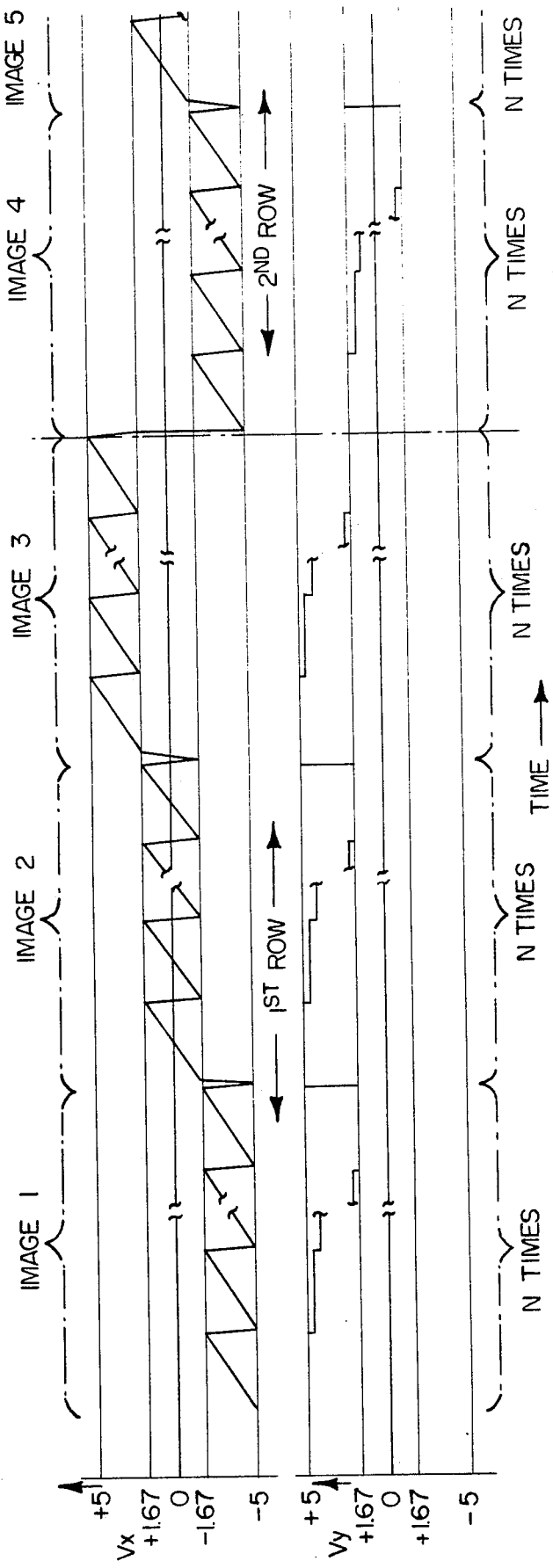
FIG. 25 is a composite graph showing horizontal and vertical TV sweeps for the first five images during automatic sequencing in the read mode.

The generation of TV read sweeps for the scan converter during automatic sequencing is illustrated in FIGS. 24 and 25. FIG. 24 is a conceptual diagram of the scan converter storage surface screen divided into nine equal areas. In order to place the electron beam at the center of the screen (i.e., in the middle of the fifth image), it is assumed that the horizontal and vertical deflection voltages must both be zero. Full horizontal deflection the left requires −5 volts and to the right +5 volts. The horizontal limits of the middle images 2, 5 and 8 are −1⅔ volts and +1⅔ volts. The full vertical deflection to the top of the screen requires +5 volts and full vertical deflection to the bottom of the screen requires −5 volts. The intermediate images 4, 5 and 6 extend in the vertical direction from +1⅔ volts to −1⅔ volts.

FIG. 25 shows two graphs: one for horizontal sweeps ($V_x$) and one for the vertical sweeps ($V_y$). The X and Y sweeps corresponding to a given image repeat N times as determined by the setting of the automatic sequencer 196 of FIG. 22.

The above described embodiment provides an efficient means for storing and displaying nine tomographic images of the heart at different points in the heart cycle without requiring a photographic step or digital storage of the image data prior to display. The timing for the entire system is efficiently carried out by derivatives of a standard TV composite sync signal, as well as the patient's ECG current. The self-test procedure inherently tests all of the major functions of the system without using a patient. Read and write modes are automatically alternated on the scan converter to permit continuous viewing of all of the images as they are being formed without stopping or losing storage. The operator also has the option of stopping the storage of information at any point by switching off the transducer ECHO signal, for example, with a foot switch, to permit trial changes in transducer location or timing settings, etc., without destroying partially formed images. In fact a change in all of the spacing and delay settings halfway through the build-up of the image is even permissible. The addition of the ECG trace with amplitude coded cursor marks in the first image space makes for easy identification of the images with the point in time during the heart cycle at which they were taken. By viewing the first image full screen, the delay and spacing intervals can be set with precision to obtain the images of the heart at the desired points of the cardiac cycle. The system also provides automatic sequential readout of the images at a rate controlled by the user. Thus, without requiring an extra processing step, this automatic sequencing enables the study of dynamic properties of the cardiac cycle to spot abnormal patterns of contraction and filling by intuitive observation.

The above described embodiment is intended to be illustrative not restrictive. For example, instead of storing the ECG waveform, any time-varying, continuous cardiac parameter can be substituted if desired for some special purpose. In addition, while nine images are preferred other numbers are of course feasible. The scope and spirit of the invention are thus defined by the appended claims and all modifications and variations which fall within the range of equivalents thereto are intended to be embraced therein.

We claim:
1. A synchronized cardiac tomographic imaging system, comprising:
   a positionable transducer means producing scan sweeps and transducer video together representing the location of cardiac structures along the axis of the transducer;
   means responsive to a beating heart for producing a repeating sync pulse indicative of the same func- tional point in each successive heart cycle;
an image timing circuit including first means to establish a delay interval between said sync pulse and a first image and second means to establish a spacing interval between each successive image;
control means responsive to said image timing circuit for generating a storage signal corresponding to the pre-established time of each image;
image counter means to count the number of storage signals issued since the sync pulse;
scan converting means having a storage matrix;
means responsive to said storage signal for causing said scan converting means to write into said matrix with said transducer video and said transducer scan sweeps for a predetermined interval of time corresponding to each one of said storage signals;
image location means responsive to said image counter means for modifying said scan sweeps to locate each image in a difference place on the storage matrix of said scan converting means;
display means; and
means for reading out to said display means the images stored in said scan converting matrix.

2. The system of claim 1, wherein said image timing circuit first and second means each include a presettable counter and a manual setting switch having a plurality of discrete states, means for inhibiting the presettable counter for the spacing interval until the other counter has finished counting the delay interval and said control means has issued a storage signal.

3. The system of claim 2, wherein said image timing circuit further includes means for clocking said counters at a rate such that the states of said switches bear a direct decimal relationship to seconds.

4. The system in claim 2, wherein said image timing circuit further includes means for clocking said presettable counter for establishing the delay interval at a rate of 100 Hz, the state of the corresponding switch being a direct indication of 100ths of a second, means for clocking the presettable counter for establishing the spacing interval at a rate of 1 KHz, the state of the corresponding switch being a direct indication of milliseconds.

5. The system of claim 4, wherein said means for 100 HZ and 1 kHz clocking are circuit means for deriving said clock frequencies from a standard TV composite sync signal.

6. The system of claim 2, wherein said image timing circuit further includes logic means for automatically sensing and incrementing said image spacing setting to the smallest possible setting if it is set to zero.

7. The system of claim 2, further comprising means for stripping the line sync signal from a TV composite sync signal, line sweep counter means for issuing a transmit signal to said transducer every $n$th line, said control means having means to gate said storage signal with said transmit signal, a timing deriving circuit receiving said line sync signal, said presettable counters being clocked by said timing deriving circuit.

8. The system of claim 7, wherein said presettable counters are connected to said timing deriving circuit so as to be clocked thereby at different rates.

9. A synchronized cardiac tomographic imaging system comprising:
a positionable transducer means producing transducer sweeps and transducer video together representing the location of cardiac structures along the axis of the transducer;
means responsive to a beating heart for producing a repeating sync pulse indicative of the same functional point in each successive heart cycle;
image timing means responsive to said sync pulse for issuing sequential storage signals indicative of a plurality of images with predetermined spacing within the heart cycle;
image counter means for counting the number of storage signals issued since the sync pulse;
a scan converting means having a storage matrix;
an auxiliary data display unit including means for generating a Y signal representing the amplitude of a continuous time-varying cardiac parameter and means for generating an X-sweep ramp signal slow enough to include more than one cycle of said cardiac parameter in one X-sweep;
a video selection circuit having a transducer video input and a constant video input;
a sweep selection circuit having a transducer sweep input and an input for the auxiliary display X and Y sweep signals;
scan converting means having a storage matrix;
image location means responsive to said image counter means for modifying the sweep output of said sweep selection circuit to said scan converting means to locate each image in a different place on the scan converting matrix;
means for controlling said selection circuits in response to said storage signal to cause said scan converting means to write into said matrix with said transducer video and transducer sweeps;
means for controlling said selection circuits and image location means on command to cause said scan converting means to write the waveform of said cardiac parameter in a predetermined image location in said matrix using said auxiliary display sweeps and constant video;
display means; and
means for reading out to said display means the images stored in said scan converting matrix.

10. The system of claim 9, further comprising means connected with said scan converting means for intermittently blanking the constant video signal when said cardiac parameter is being written.

11. The system of claim 9, wherein said auxiliary display unit further includes analog summing means responsive to said image timing circuit for adding pulses to said Y signal coincident with said storage signals to provide cursors on the cardiac waveform.

12. The system of claim 11, wherein said analog summing means is further responsive to said image counter means for enhancing the amplitude of certain ones of the cursors.

13. A synchronized cardiac tomographic imaging system, comprising:
a positionable transducer means producing scan sweeps and transducer video together representing the location of cardiac structures along the axis of the transducer;
means responsive to a beating heart for producing a repeating sync pulse indicative of the same functional point in each successive heart cycle;
image timing means responsive to said sync pulse for issuing sequential storage signals indicative of a plurality of images with predetermined spacing within the heart cycle;
image counter means for counting the number of storage signals issued since the sync pulse;

scan converting means having a storage matrix;
a video selection circuit having a transducer video input and a constant video input;
a TV sweep generator connected to receive a TV composite sync signal;
a sweep selection circuit having a transducer sweep input and a TV sweep input;
image location means responsive to said image counter means for modifying the sweep output of said sweep selection circuit to said scan converting means to locate each image in a different place of said scan converting matrix;
means for controlling said selection circuits in response to said storage signal to cause said scan converting means to write into said matrix with said transducer sweeps and transducer video;
self-test means for controlling said selection circuits on command to cause said scan converting means to write into said matrix with said TV sweeps and constant video in response to said storage signals, said constant video being gated on for a predetermined interval by said storage signal resulting in one horizontal bar per image location on said scan converting matrix, spaced vertically in accordance with the predetermined spacing of said image timing means;
display means; and
means for reading out to said display means the images stored in said scan converting matrix.

14. The system of claim 13, wherein said display means is a TV receiver and said scan converting means is read out to said receiver using said TV sweeps.

15. The system of claim 13, further comprising means for generating a fake cardiac sync pulse on command.

16. The system of claim 15, further comprising means responsive to said image counter means to trigger said fake pulse generator after the counting of the last image.

17. The system of claim 13, further comprising a binary counter enabled by said self-test means and clocked by a derivative of said TV composite sync signal for producing a fake cardiac sync pulse.

18. The system of claim 17, further comprising:
means responsive to said image counter means for resetting said binary counter after producing a fake pulse until the last image has been counted.

19. A synchronized cardiac tomographic imaging system comprising:
a positionable transducer means producing transducer sweeps and transducer video together representing the location of cardiac structures along the axis of the transducer;
means responsive to a beating heart for producing a repeating sync pulse indicative of the same functional point in each successive heart cycle;
image timing means responsive to said sync pulse for issuing sequential storage signals indicative of a plurality of images with predetermined spacing within the heart cycle;
Image counter means for counting the number of storage signals issued since the sync pulse.
an electronic scanner;
means responsive to said storage signal for gating said transducer scan sweeps and transducer video to said electronic scanner;
image location means responsive to said image counter means for modifying said transducer scan sweeps to locate each image; and
means for detecting the overrun condition where a sync pulse occurs before the last image is counted by said counter means.

20. A synchronizing cardiac tomographic imaging system, comprising:
a positionable transducer means producing transducer scan sweeps and transducer video together representing the location of cardiac structures along the axis of the transducer;
means responsive to a beating heart for producing a repeating sync pulse indicative of the same functional point in each successive heart cycle;
image timing means responsive to said sync pulse for issuing sequential storage signals indicative of a plurality of images with predetermined spacing within the heart cycle;
image counter means for counting the number of storage signals issued since the sync pulse;
TV sweep generating means connected to receive a TV composite sync signal;
scan converting means with a storage matrix;
a scan sweep selection circuit having a transducer input and a TV sweep input;
means connected with said selection circuit for causing said scan converter to write into its storage matrix with transducer sweeps and transducer video in response to said storage signals;
image location means responsive to said image counter means for modifying the sweep output of said sweep selection circuit to said scan converting means to locate each image in a different place on the storage matrix;
TV receiver connected to receive the video output of said scan converting means;
means for causing said selection circuit to apply TV sweeps to said scan converter in the read mode via said image location means to provide a video output to said TV receiver; said TV receiver having means responsive to said TV composite sync signal for generating its own TV sweeps; and
means for simulating the output of said image counter means to said image location means at a controlled rate to provide sequencing through the images during the read mode to effect animation.

21. The system of claim 20, wherein said simulating means includes means for dividing the frequency of a vertical sync signal derived from said TV composite sync signal by N, means for repeatedly counting the divided output up to the highest number of images, the image location circuit being responsive to the resulting frame count in the same manner as to the image count during image build-up.

22. The system of claim 21, wherein said simulating means further includes rate control means for setting N.

23. A synchronized cardiac tomographic imaging system comprising:
a positionable transducer means producing transducer sweeps and transducer video together representing the location of cardiac structure along the axis of the transducer;
means responsive to a beating heart for producing a repeating sync pulse indicative of the same functional point in each successive heart cycle;